(12) United States Patent
Apicella et al.

(10) Patent No.: US 7,309,600 B2
(45) Date of Patent: Dec. 18, 2007

(54) HAEMOPHILUS INFLUENZAE SIALYLTRANSFERASE AND METHODS OF USE THEREOF

(75) Inventors: Michael A. Apicella, Solon, IA (US); Bradford W. Gibson, Berkeley, CA (US); Nancy J. Phillips, Berkeley, CA (US); Paul A. Jones, Coralville, IA (US); Nicole M. Samuels, Oakland, CA (US)

(73) Assignee: University of Iowa Research Foundation, Iowa City, IA (US)

( * ) Notice: Subject to any disclaimer, the term of this patent is extended or adjusted under 35 U.S.C. 154(b) by 97 days.

(21) Appl. No.: 10/366,548

(22) Filed: Feb. 12, 2003

(65) Prior Publication Data

US 2004/0156837 A1    Aug. 12, 2004

(51) Int. Cl.
C12N 1/20      (2006.01)
C12N 15/00     (2006.01)
C07H 21/02     (2006.01)
C07H 21/04     (2006.01)
C12N 9/10      (2006.01)

(52) U.S. Cl. .............................. 435/252.3; 435/252.33; 435/320.1; 435/193; 536/23.1; 536/23.2; 536/23.7

(58) Field of Classification Search ...................... None
See application file for complete search history.

(56) References Cited

U.S. PATENT DOCUMENTS 5,180,674 A    1/1993   Roth
6,210,933 B1   4/2001   Gilbert et al. ................ 435/97

FOREIGN PATENT DOCUMENTS

WO    WO 93/13198    7/1993
WO       00/70060  * 11/2000

OTHER PUBLICATIONS

Phillips et al. (2000) J Biol Chem 275:4747-4758.*
Phillips et al. (2002) J Biol Chem 277:14598-14611.*
Database GenBank Accession No. AY061634, Apr. 2002.*
Hood et al. (1996) Mol Microbiol 22:951-965.*
Brenner (1999) Trends Genet 15:132-133.*
"Introduction to Protein Structure," Branden and Tooze, Garland Publishing Inc., New York, 1991, p. 247.*
Witkowski et al., Biochemistry 38:11643-11650, 1999.*
Dyck et al., Trends Biotechnol 21:394-399, 2003.*
Vain et al., Theor Appl Genet 105:878-889, 2002.*
Dictionary definition of "can" at Encarta.msn.com, last viewed on Apr. 13, 2007.*
Dictionary definition of "native" at Encarta.msn.com, last viewed on Apr. 13, 2007.*

Moran, Anthony.P. ,et al. ,"Molecular mimicry of host structures by bacterial lipopolysaccharides and its contribution to disease", *FEMS Immunology and Medical Microbiology*, vol. 16, pp. 105-115 (1996).
"CMP-N-acetylneuraminate-beta-galactosamide-alpha-2,3-sialytransferase" [online]. National Center for Biotechnology Information, Dec. 3, 2005, [retrieved on Jan. 16, 2006]. <URL:http://www.ncbi.nlm.nih.gov/entrez/viewer.fcgi?db=protein&val=68250303>.
"Hypothetical protein Hflu203001141" [online]. National Center for Biotechnology Information, Oct. 1, 2004, [retrieved on Jan. 16, 2006]. <URL: http://www.ncbi.nlm.nih.gov/entrez/viewer.fcgi?db=protein&val=46133607).
"Hypothetical protein Hflu103001488" [online]. National Center for Biotechnology Information, Oct. 1, 2004, [retrieved on Jan. 16, 2006]. <URL: http://www.ncbi.nlm.nih.gov/entrez/viewer.fcgi?db=protein&val=42629050>.
"Hypothetical protein PM0508" [online]. National Center for Biotechnology Information, Dec. 3, 2005, [retrieved on Jan. 16, 2006]. <URL: http://www.ncbi.nlm.nih.gov/entrez/viewer.fcgi?db=protein&val=15602373>.
"CMP-N-acetylneuraminate-beta-galactosamide-alpha-2,3-sialyltransferase" [online]. National Center for Biotechnology Information, Jan. 9, 2006, [retrieved on Jan. 16, 2006]. <URL: http://www.ncbi.nlm.nih.gov/entrez/viewer:fcgi?db=protein&val=15794065>.
"*Haemophilus influenzae* lsg locus" [online] National Center for Biotechnology Information, Apr. 26, 1993, [retrieved on Aug. 29, 2006]. <URL: http://www.ncbi.nlm.nih.gov/entrez/viewer.fcgi?db=nuccore&val=148931>.
"ORF 2" [online]. National Center for Biotechnology Information, Apr. 26, 1993, [retrieved on Nov. 14, 2002]. <URL: http://www.ncbi.nlm.nih.gov/entrez/viewer.fcgi?db=protein&val=148933>.
Abdillahi and Poolman, *FEMS Microbiology Letters*, 48:367-371 (1987).
Alexeyev, *Biotechniques*, 18:52-56 (1995).
Altschul et al., *Nucleic Acids Res.* 25:3389-3402 (1997).
Altschul et al., *J. Mol. Biol.*, 215:403-410 (1990).
Aspinall et al., *Infection & Immunity*, 62:2122-2125 (1994).
Borovkov et al., *Biotechniques*, 22:812-814 (1997).
Bozue et al., *Journal of Biological Chemistry*, 274:4106-4114 (1999).
Campagnari et al., *Infection & Immunity*, 55:882-887 (1987).
Cope et al., *Infection & Immunity*, 58:2343-2351 (1999).
Corpet et al., *Nucl. Acids Res.*, 16:10881-10890 (1988).
Edwards et al., *Molecular Microbiology*, 14:141-149 (1994).
Fleischmann et al., *Science*, 269:496-512 (1995).
Gibson et al., *Journal of American Society for Mass Spectromery*, 8:645-658 (1997).
Gilbert et al., *European Journal of Biochemistry*, 249:187-194 (1997).

(Continued)

*Primary Examiner*—David J. Steadman
(74) *Attorney, Agent, or Firm*—Viksnins Harris & Padys PLLP

(57) ABSTRACT

The present invention is directed to sialytransferases, such as SiaA sialytransferases isolated from *Haemophilus influenzae*. Further provided herein are methods for producing sialylated lipooligosaccharides, vaccines, and host cells and systems for the production of sialylated lipooligosaccharides.

15 Claims, 4 Drawing Sheets

OTHER PUBLICATIONS

Gilbert et al., *Journal of Biological Chemistry*, 271:28271-28276 (1996).
Gilbert et al., *Journal of Biological Chemistry*, 275:3896-3906 (2000).
Goeddel, "Systems for heterologus gene expression" *Methods in Enzymology*, Academic Press, San Diego, Calif. (1990) 185:3-7.
Guerry et al., *Infection & Immunity*, 68:6656-6662 (2000).
Herriott et al., *Journal of Bacteriology*, 101:517-524 (1970).
Higgins et al., *Gene*, 73:237-244 (1988).
Higgins et al., *CABIOS*, 5:151-153 (1989).
Hitchcock et al., *Journal of Bacteriology*, 154:269-277 (1983).
Hood et al., *Molecular Microbiology*, 33:679-692 (1999).
Hood et al., *Molecular Microbiology*, 39:341-350 (2001).
Huang et al., *CABIOS*, 8:155-165 (1992).
Inzana, *Journal of Infectious Diseases*, 148:492-499 (1983).
Jones et al. *J. Biol. Chem.* 277(17):14598-14611 (2002).
Karlin et al., *Proc. Natl. Acad. Sci. USA*, 87:2264-2268 (1990).
Karlin et al., *Proc. Natl. Acad. Sci. USA*, 90:5873-5877 (1993).
Kimura et al., *Infection & Immunity*, 51:69-79 (1986).
Kimura et al., *Infection & Immunity*, 55:1979-1986 (1987).
Lesse et al., *Journal of Immunological Methods*, 126:109-117 (1990).
Mandrell et al., *Infection & Immunity*, 60:1322-1328 (1992).
Mandrell et al., *Journal of Experimental Medicine*, 168:107-126 (1988).
Maskell et al., *Molecular Microbiology*, 5:1013-1022 (1991).
Masoud et al, *Biochemistry*, 36:2091-2103 (1997).
Menard et al., *Journal of Bacteriology*, 175:5899-5906 (1993).
Moran et al., *Journal of Bacteriology*, 173:618-626 (1991).
Myers et al., *CABIOS*, 4:11-17 (1988).
Nairn et al., *Journal of General Microbiology*, 134:3295-3306 (1988).
Needleman, et al., *J. Mol. Biol.* 48:443-453 (1970).
Parsons et al., *Microbial Pathogenesis*, 14:329-335 (1993).
Parsons et al., *Microbial Pathogenesis*, 5:303-309 (1988).
Patrick et al., *Infection & Immunity*, 55:2902-2911 (1987).
Pearson et al., *Meth. Mol. Biol.*, 24:307-331 (1994).
Pearson et al., *Proc. Natl. Acad. Sci. USA*, 85:2444-2448 (1988).
Phillips et al., *Biochemistry* 32:2003-2012 (1993).
Phillips et al., *Biochemistry*, 35:5937-5947 (1996).
Prendergast et al., *Infection & Immunity*, 66:3649-3655 (1998).
Preston et al., *Crit Rev Microbiol* 22(3):139-180 (1996).
Risberg et al., *European Journal of Biochemistry* 261:171-180 (1990).
Schauer, *Methods in Enzymology*, 50:64-89 (1987).
Schauer, *Advances in Carbohydrate Chemistry and Biochemistry*, 40:131-234 (1982).
Schneider et al., *Journal of Experimental Medicine*, 174:1601-1605 (1991).
Smith et al., *Adv. Appl. Math.*, 2:482-489 (1981).
Spinola et al., *Infection & Immunity*, 58:1558-1564 (1990).
Swords et al., *Molecular Microbiology*, 37:13-27 (2000).
Towbin et al., *Proc. Natl. Acad. Sci. USA*, 76:4350-4354 (1979).
Tsai et al., *Analytical Biochemistry*, 119:115-119 (1982).
Vimr et al., *Molecular Microbiology*, 36:1113-1123 (2000).
Weiser et al., *Cell*, 59:657-665 (1989).
Weiser et al., *Infection & Immunity*, 57:3045-3052 (1989).
Weiser et al., *Journal of Bacteriology*, 172:3304-3309 (1990).
Whitby et al., *FEMS Microbiology Letters*, 158:57-60 (1998).
Yamasaki et al., *Molecular Immunology*, 28:1233-1242 (1991).
Zwahlen et al., *Microbial Pathogenesis*, 1:465-473 (1986).

\* cited by examiner

HAEMOPHILUS INFLUENZAE SIALYLTRANSFERASE AND METHODS OF USE THEREOF

STATEMENT OF GOVERNMENT RIGHTS

The invention described herein was made with government support under Grant Number A124616, A165298 and A131254 awarded by the National Institute of Allergy and Infectious Diseases. The United States Government has certain rights in the invention.

BACKGROUND OF THE INVENTION

*Haemophilus influenzae* frequently colonizes the human nasopharynx. Up to 80% of the population harbor this organism as part of their normal flora. Although normally an innocuous inhabitant of the upper respiratory tract, *H. influenzae* is an opportunistic pathogen. The diseases caused by the organism can be ordered in two groups based on the presence or absence of a capsule.

Encapsulated or typeable organisms, which range from capsule types a-f, can cause systemic infections such as bacteremia, septicemia, and bacterial meningitis. Of the various encapsulated types, *H. influenzae* type b (Hib) has been associated most often with pathogenesis. The non-encapsulated or non-typeable (NTHi) strains of *H. influenzae* cause more localized infections, such as chronic bronchitis or otitis media, and rarely cause systemic infections.

There are a number of virulence factors associated with both Hib and NTHi that contribute to their pathogenesis, one of these being the lipooligosaccharide (LOS). LOS is a complex glycolipid containing three main regions: lipid A, core, and a variable branched region. The core region is a conserved structure containing a phosphorylated 2-keto-3-deoxy-D-manno-octulosonic acid (Kdo) residue linked to three heptose residues, while the variable branched region contains a heterogeneous mix of hexoses and N-acetylhexosamines as well as other factors, such as phosphoethanolamine (PEA), phosphorylcholine, and N-acetylneuraminic acid (NeuAc, also known as sialic acid or SA).

LOS sialylation is believed to influence aspects of susceptibility of a particular bacterial organism to the defense mechanism of a host, e.g., resistance to phagocytosis by neutrophils, the ability of a bacterium to invade a host cell, as well as resistance to the antibody-complement dependent bactericidal effect of serum. The sialylation of LOS is catalyzed by enzymes referred to as sialyltransferases, which are glycosyltransferases. A sialyltransferase catalyzes the transfer of sialic acid (SA) to terminal portions of carbohydrate groups found, for example, on glycolipids and oligosaccharides.

Glycosyltransferases, including sialyltransferases, can be used in vitro to prepare oligosaccharides and polysaccharides (see, e.g., U.S. Pat. Nos. 5,180,674 and 6,210,933). The advantage of biosynthesis with glycosyltransferases is that the glycosidic linkages formed by enzymes are highly stereo and regio-specific. However, each enzyme catalyzes linkage of specific sugar residues to other specific acceptor molecules. Thus, synthesis of a desired oligosaccharide is limited by the availability of glycosyltransferases (see, Roth, International Patent Publication No. WO 93/13198, published Jul. 8, 1993).

There remains a need in the art for the identification and isolation of bacterial sialyltransferases, in particular, sialyltransferases from *H. influenzae*. Moreover, there remains a need in the art for a method of producing sialylated *H. influenzae* lipooligosaccharides, e.g., for the production of vaccines against *H. influenzae*.

SUMMARY OF THE INVENTION

The present invention provides an isolated polynucleotide having SEQ ID NO:1, wherein SEQ ID NO:1 encodes a sialyltransferase. For example, the polynucleotide can include nucleotides 2538-3452 of SEQ ID NO:1. The invention further provides an isolated SiaA sialyltransferase encoded by a polynucleotide having SEQ ID NO:1, such as nucleotides 2538-3452 of SEQ ID NO:1. The invention also provides a polypeptide that can include SEQ ID NO:3, wherein the polypeptide is SiaA sialyltransferase.

The invention also provides an isolated SiaA sialyltransferase, for example, from *Haemophilus influenzae*, such as *H. influenzae* strain 2019, strain A2, strain Rd, strain 7502 or strain 3198.

Further provided is a method for producing a sialylated lipooligosaccharide(LOS), such as *H. influenzae* LOS, which method involves contacting an acceptor molecule, such as a complex carbohydrate, e.g., Galβ1-4GlcNAc-Galβ1-4GlcNac-R, wherein R is a lipid, a glycolipid, a lipoprotein, or a polysaccharide, with N-acetylneuraminic acid in the presence of a sialyltransferase, wherein the sialyltransferase is SiaA or LsgB, such that N-acetylneuraminic acid binds to the acceptor molecule. The LsgB sialyltransferase can have SEQ ID NO:4. The LOS can include a terminal N-acetyllactosamine. The complex carbohydrate can be, for example, a chimeric carbohydrate, such as one produced by contacting a core lipid structure having a terminal heptose molecule with an enzyme capable of adding an acceptor molecule to the heptose molecule. The SiaA sialyltransferase can have SEQ ID NO:3. Also provided is a sialylated LOS produced by such a method, and a vaccine with such a sialylated LOS.

The invention further provides an expression cassette having an isolated polynucleotide of the invention, a cell transformed with such an expression cassette, such as a host cell. A cell can also include an expression cassette having a nucleotide sequence encoding LsgB sialyltransferase. A cell of the invention can be a LOS production cell, with a lipooligosaccharide synthesis genes (lsg) locus, e.g., lsgB, an expression cassette of the invention, an acceptor molecule and a substrate for a sialyltransferase. The production cell can also include an expression cassette including a nucleotide sequence encoding a LsgB sialyltransferase, e.g., LsgB having SEQ ID NO:4. The production cell can be a gram negative bacterium, such as *H. influenzae* or *E. coli*.

The invention further provides a method of producing a sialylated *H. influenzae* LOS comprising a production cell of the invention.

DETAILED DESCRIPTION OF THE INVENTION

I. Definitions

Figure 1:
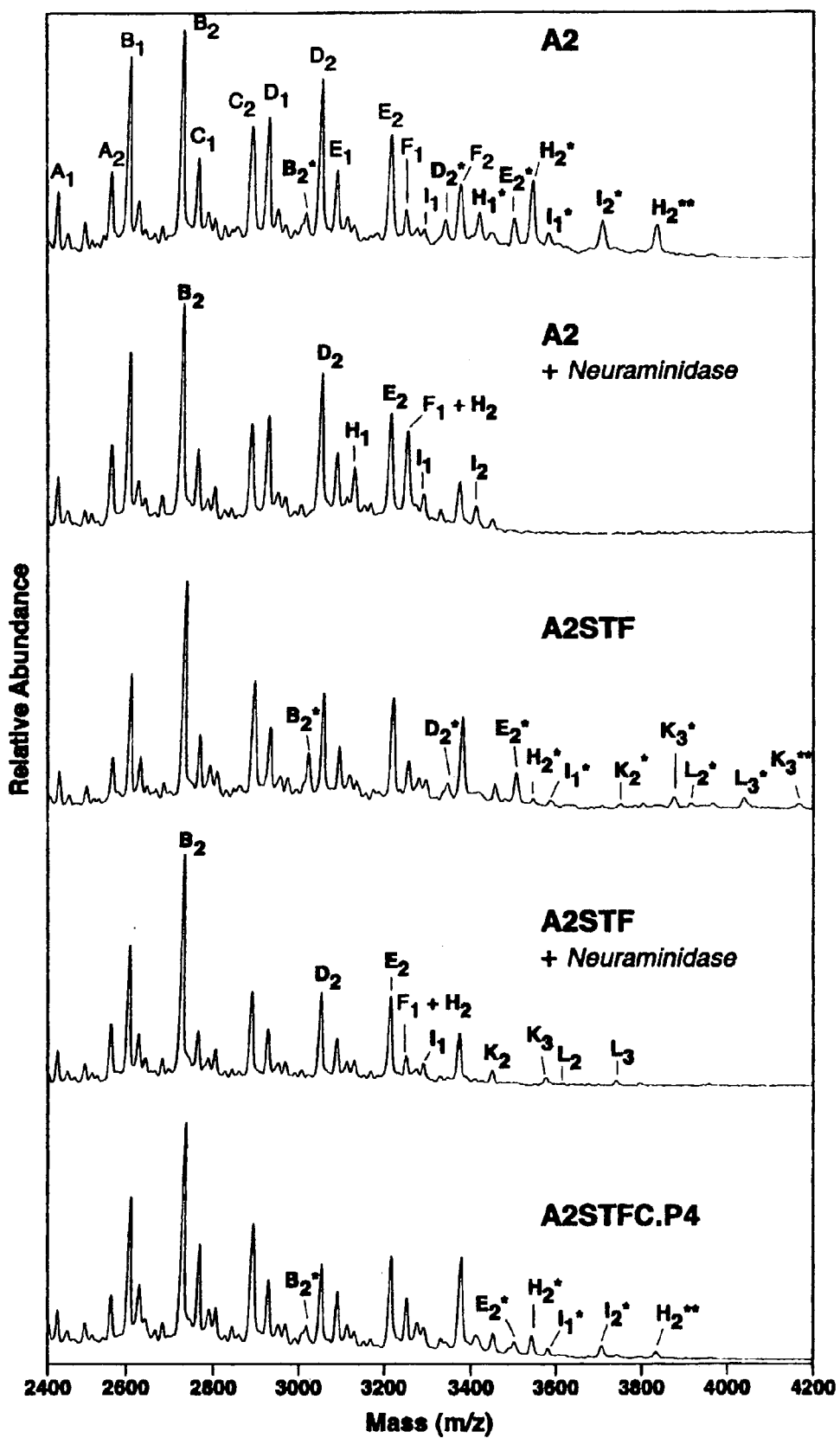
FIG. 1 depicts negative ion MALDI-MS spectra of O-LOS from *H. influenzae* A2, A2STF, and A2STFC.P4. Mass spectra are shown comparing LOS isolated from *H. influenzae* strains before and after treatment with neuraminidase. See Tables 2 and 3 for molecular weights and compositions. The asterisks indicate the addition of NeuAc, and the number of PEA moieties is denoted by subscript.

The term "acceptor molecule" refers to any molecule onto which a sialyltransferase of the invention can transfer a sialic acid residue. An acceptor molecule can be, for example, a glycoprotein, lipid, glycolipid or oligosaccharide, or a terminal carbohydrate group thereof. An acceptor molecule of the invention can be a "complex carbohydrate," such as Gal β1-4GlcNAc-Galβ1-4GlcNac-R, where R is a lipid, a glycolipid, a lipoprotein, or a polysaccharide, or a "chimeric carbohydrate".

A "complex carbohydrate" is a chemical compound having the general formula $(CH_2O)_n$, wherein the monomer unit is selected from any naturally occurring or synthetic monomer, including, but not limited to, glucose, galactose, mannose, fucose and sialic acid. Saccharides may have additional constituents such as amino, sulfate or phosphate groups, in addition to the carbon-hydrogen-oxygen core. A polymer consisting of two to ten saccharide units is termed an oligosaccharide (OS). A polymer consisting of more than ten saccharide units is termed a polysaccharide (PS). These monosaccharide building blocks can be linked in at least ten different ways, leading to a number of different combinations and permutations. Examples of complex carbohydrates include the complex carbohydrates of Gram-negative bacteria, which are linked to lipids to form lipooligosaccharides (LOS) or lipopolysaccharides (LPS). LOS differs from LPS in that the variable branched region, or O-antigen, is a non-repeating unit.

"Chimeric carbohydrate" refers to a carbohydrate containing subunits not normally found in nature, or not naturally adjoined. For example, a chimeric carbohydrate is a lipooligosaccharide (LPS) produced by a bacterium that has been transfected with a plasmid containing an heterologous gene involved in the synthesis of a carbohydrate epitope specific to a different bacterium. By way of illustration, an *E. coli* that normally synthesizes a rough LPS may be transfected with a plasmid containing a heterologous gene involved in the synthesis of a carbohydrate epitope, for example, a *H. influenzae* gene, such that the *E. coli* produces a chimeric carbohydrate. The term "heterologous gene" refers to a nucleic acid sequence that originates from a source foreign to the particular host cell, or, if from the same source, a nucleic acid sequence that has been modified from its original form. A chimeric carbohydrate can be produced by contacting a "core lipid structure" having a terminal heptose molecule with an enzyme capable of adding an acceptor molecule to the heptose molecule, e.g., a sialyltransferase. A "core lipid structure" is a portion of a LOS having conserved structure, and containing a phosphorylated 2-keto-3-deoxy-D-manno-octulosonic acid (Kdo) residue linked to three heptose residues.

A donor substrate for the sialyltransferases of the invention include activated nucleotide sugars that further contain a sialic acid residue. For example, in the case of N-acetylneuraminic acid (NANA), the activated sugar is cytidine monophosphate (CMP)-NANA.

A "sialyltransferase" of the invention is a glycosyltransferase that catalyzes the sialylation of an acceptor molecule. "SiaA sialyltransferase" refers to a sialyltransferase isolated from a *H. influenzae*, wherein the SiaA sialyltransferase has an amino acid sequence containing SEQ ID NO:3, e.g., an amino acid sequence encoded by SEQ ID NO:1. SEQ ID NO:1 and SEQ ID NO:3 have been deposited in GenBank (accession nos. AY061634 and AAL38659.1, respectively). Nucleotides 2538-3452 of SEQ ID NO:1, i.e., SEQ ID NO:2, make up the coding sequence for the SiaA sialyltransferase. SiaA sialyltransferase can be isolated using techniques known to the art from any strain of *H. influenzae*, e.g., 2019, A2 and Rd. "LsgB sialyltransferase" refers to a sialyltransferase isolated from *H. influenzae* having an amino acid sequence SEQ ID NO:4 (GenBank accession no. Q48211).

As used herein, the term "nucleic acid" refers deoxyribonucleotides or ribonucleotides and polymers thereof in either single- or double-stranded form, composed of monomers (nucleotides) containing a sugar, phosphate and a base that is either a purine or pyrimidine. The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

The invention encompasses isolated or substantially purified nucleic acid or protein compositions (the terms "protein," "peptide" and "polypeptide" are used interchangeably herein). In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell.

"Recombinant" polypeptides refer to polypeptides produced by recombinant DNA techniques, i.e., produced from cells transformed by an exogenous DNA construct encoding the desired polypeptide. "Synthetic" polypeptides are those prepared by chemical synthesis. "Recombinant DNA molecule" is a combination of DNA sequences that are joined together using recombinant DNA technology and procedures used to join together DNA sequences as described (for example, as in Sambrook and Russell, 2001).

The term "gene" is used broadly to refer to any segment of nucleic acid associated with a biological function. Thus, genes include coding sequences and/or the regulatory sequences required for their expression.

"Naturally occurring," "native" or "wild type" is used to describe an object that can be found in nature as distinct from being artificially produced. Furthermore, "wild-type" refers to the native gene without any known mutation. "Native" or "wild type" proteins, polypeptides or peptides are proteins, polypeptides or peptides isolated from the source in which the proteins naturally occur.

The term "chimeric" refers to any gene or DNA that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

"Homology" refers to the percent identity between two polynucleotide or two polypeptide sequences. Two DNA or polypeptide sequences are "homologous" to each other when the sequences exhibit at least about 75% to 85%, at least about 90%, or at least about 95% to 98% contiguous sequence identity over a defined length of the sequences.

The following terms are used to describe the sequence relationships between two or more nucleic acids or polynucleotides: (a) "reference sequence," (b) "comparison window," (c) "sequence identity," (d) "percentage of sequence identity," and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, *CABIOS*, 4:11 (1988); the local homology algorithm of Smith et al., *Adv. Appl. Math.*, 2:482 (1981); the homology alignment algorithm of Needleman and Wunsch, *JMB*, 48:443 (1970); the search-for-similarity-method of Pearson and Lipman, *Proc. Natl. Acad. Sci. USA*, 85:2444 (1988); the algorithm of Karlin and Altschul, *Proc. Natl. Acad. Sci. USA*, 87:2264 (1990), modified as in Karlin and Altschul, *Proc. Natl. Acad. Sci. USA*, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988); Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994). The ALIGN program is based on the algorithm of Myers and Miller, supra. The BLAST programs of Altschul et al., *JMB*, 215: 403 (1990); *Nucl. Acids Res.*, 25:3389 (1990), are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or less than about 0.001.

To obtain gapped alignments for comparison purposes, Gapped BLAST (in BLAST 2.0) can be utilized as described in Altschul et al., *Nucleic Acids Res.* 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein can be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, or at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or at least 95%.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones having a population of daughter cells containing the exogenous DNA.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

A "host cell" is a cell which has been transformed, or is capable of transformation, by an exogenous nucleic acid molecule. Thus, "transformed," "transgenic," and "recombinant" refer to a host cell or organism into which a heterologous nucleic acid molecule has been introduced. The nucleic acid molecule can be stably integrated into the genome generally known in the art and are disclosed in Sambrook and Russell, 2001. For example, "transformed," "transformant," and "transgenic" cells have been through the transformation process and contain a foreign gene integrated into their chromosome. The term "untransformed" refers to normal cells that have not been through the transformation process.

A "production cell" refers to a cell that contains a acceptor molecule, a donor substrate containing N-acetylneuraminic acid, and a sialyltransferase such as SiaA and/or LsgB, for the production of sialylated *H. influenzae* LOS. As an example, sialyltransferases can be introduced into the production cell via transformation with expression cassettes containing DNA encoding a SiaA and/or LsgB sialyltransferase. Similarly, cells that are otherwise suitable but lack the proper acceptor molecule may be used as production cells if they are co-transformed with genes for complex carbohydrate formation.

"Expression cassette" as used herein means a DNA sequence capable of directing expression of a particular nucleotide sequence in an appropriate host cell or production cell, comprising a promoter operably linked to the nucleotide sequence of interest which is operably linked to termination signals. It also typically includes sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will have the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source.

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Genome" refers to the complete genetic material of an organism.

A "vector" is a replicon, such as a plasmid, phage, virus, or cosmid, to which another DNA segment may be attached so as to bring about the replication of the attached segment. A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "regulatory sequence" is art-recognized and intended to include promoters, enhancers and other expression control elements (e.g., polyadenylation signals). Such regulatory sequences are known to those skilled in the art and are described in Goeddel, Gene Expression Technology: *Methods in Enzymology*, 185, Academic Press, San Diego, Calif. (1990). It should be understood that the design of the expression vector may depend on such factors as the choice of the host cell to be transfected and/or the amount of fusion protein to be expressed.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal" or "core" promoters. In the presence of a suitable transcription factor, the minimal promoter functions to permit transcription. A "minimal" or "core" promoter thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

The term DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

A control element, such as a promoter, "directs the transcription" of a coding sequence in a cell when RNA polymerase will bind the promoter and transcribe the coding sequence into mRNA, which is then translated into the polypeptide encoded by the coding sequence.

"Operably-linked" refers to the association of nucleic acid sequences on single nucleic acid fragment so that the function of one is affected by the other, e.g. an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

"Expression" refers to the transcription and/or translation of an endogenous gene or a transgene in cells. Expression may also refer to the production of protein.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

II. Sialyltransferases of the Invention

Sialyltransferases are a group of glycosyltransferases that transfer sialic acid from an activated sugar nucleotide to acceptor oligosaccharides found on glycoproteins, glycolipids or polysaccharides. Sialylated oligosaccharides play important roles in cell-cell recognition, cell differentiation and various receptor-ligand interactions in mammalian systems.

Sialyltransferases of the invention can be isolated from any strain of H. influenzae, for example, from H. influenzae strains 2019, 7502, 3198, A2 and Rd. In addition to the methods described herein, those of skill in the art of molecular biology generally know methods for isolating the H. influenzae sialyltransferases of the invention, for example, see Sambrook and Russell (2001), incorporated herein by reference.

As an example, GenBank accession number AAL38659 (SEQ ID NO:3) describes a SiaA sialyltransferase isolated from H. influenzae strain A2.

The sialyltransferases of the invention can be used to add sialic acid residues of different forms to acceptor molecules. Typically, the sialic acid is 5-N-acetylneuraminic acid, (NeuAc) or 5-N-glcolylneuraminic acid (NeuGc). Other sialic acids may be used in their place, however. For a review of different forms of sialic acid suitable in the present invention see, Schauer, *Methods in Enzymology*, 50, 64-89 (1987), and Schaur, *Advances in Carbohydrate Chemistry and Biochemistry*, 40, 131-234 (1982).

III. Methods of the Invention

The invention provides methods of using sialyltransferases such as SiaA sialyltransferase. The methods that produce sialylated LOS of the invention take place in a medium containing at least one sialyltransferase, a donor substrate, and an acceptor sugar. The methods rely on the use of the sialyltransferase to catalyze the addition of a saccharide, e.g., NANA, to a complex carbohydrate. For example, the invention provides methods for adding sialic acid to a complex carbohydrate by contacting a mixture comprising an activated sialic acid (e.g., CMP-NANA) to an acceptor moiety comprising a Gal residue in the presence of a sialyltransferase that has been prepared according to the methods described herein. For example, a complex carbohydrate, such as H. influenzae LOS, can be sialyated by contacting an acceptor molecule with N-acetylneuraminic acid in the presence of a sialyltransferase, e.g., a SiaA and/or a LsgB.

The sialyltransferase prepared as described herein can be used in combination with additional glycosyltransferases. For example, a combination of sialyltransferase and galactosyltransferases can be used.

In accordance with one embodiment of this invention, sialylated H. influenzae LOS is produced from a production cell by transforming the cell with a recombinant DNA molecule comprising an expression cassette.

The products produced by the above processes can be used without purification. However, standard techniques for recovery of glycosylated saccharides such as thin or thick layer chromatography, partition chromatography, ion exchange chromatography, or membrane filtration can be used. It is preferred to use membrane filtration, utilizing a reverse osmotic membrane, or one or more column chromatographic techniques for the recovery. For instance, membrane filtration wherein the membranes have molecular weight cutoff of about 3000 to about 10,000 can be used to remove proteins. Nanofiltration or reverse osmosis can then be used to remove salts. Nanofilter membranes are a class of reverse osmosis membranes which pass monovalent salts but retain polyvalent salts and uncharged solutes larger than about 100 to about 700 Daltons, depending upon the membrane used.

EXAMPLE 1

Introduction

*H. influenzae* LOS is very heterogeneous and contains a number of phase-varying epitopes (Inzanna, 1983; Patrick, 1987). Phase-variation is known at least in part to occur through a process of slipped-strand mispairing (Weiser et al. 1). Three well characterized loci involved in LOS expression and phase-variation, designated lic1, lic2, and lic3, phase-vary through this mechanism (Maskell et al., 1991; Weiser et al., II). Phase-variation may play a role for the bacterium in the evasion of the host immune response. LOS structures have also been found to mimic human blood group antigens, such as the $P^k$ antigen and paragloboside (Mandrell et al., 1992). This may be another method for bacterial immune evasion.

The lsg (lipooligosaccharide synthesis genes) locus is another region involved in LOS biosynthesis (Spinola et al., 1990). Seven genes are in the locus, six of which have identity to various glycosyltransferases and one gene that acts as a regulator (Phillips et al., 2000). This locus is not controlled by the slipped-strand mispairing mechanism. Through studies expressing chimeric *Haemophilus* structures in *Escherichia coli* LPS, this locus is known to be involved in the expression of a terminal N-acetyllactosamine structure (Phillips et al., 2000). One of the genes in this locus, lsgB, has homology (27% identity, 46% similarity) to the sialyltransferase in *Neisseria meningitidis*. In various *Neisseria* and *Haemophilus* species, a terminal N-acetyllactosamine structure has been shown to be an acceptor for sialylation (Mandrell et al., 1992; Phillips et al., 1996; and Mandrell et al., 1988).

NeuAc is a constituent of the LOS in about half of the *H. influenzae* strains tested (Mandrell et al., 1992; Hood et al., 1999). Sialylation in *H. influenzae* has been shown to affect its ability to evade the lytic effects of human serum (Hood et al., 1999; Hood et al., 2001). Two genes have been identified that are involved in LOS sialylation; siaB and lic3A (Id.). siaB is a CMP-NeuAc synthetase, and a mutation in this gene eliminates all sialylation (Hood et al., 1999). The second gene, lic3A, has been shown to function as an α2-3-sialyltransferase, responsible for sialylating terminal lactose structures. The lic3A gene has about 40% identity to cstII from *Campylobacter jejuni* (Hood et al., 2001). This gene is one of two sialyltransferases identified in this organism (Gilbert et al., 2000). A mutation in lic3A in one strain of *H. influenzae* still contained sialylated glycoforms, indicating the possibility of a second sialyltransferase in this organism (Hood et al., 2001). *H. influenzae* contains a homologue to a sialyltransferase from *H. ducreyi*, which is designated as HI0871 in the *H. influenzae* Rd genome database (Fleischmann et al., 1995). In a study looking at a number of genes from *H. influenzae* and their possible role in LOS biosynthesis, no function for this gene (designated orfY) was found (Hood et al., 1996). This gene, referred to herein as siaA, was studied for its possible role in LOS sialylation. Evidence that siaA is a sialyltransferase in *H. influenzae* and that lsgB is required for the biosynthesis of a third, distinct sialylated glycoform is reported herein. LsgB was found to be the third sialyltransferase.

Materials and Methods

Bacterial Strains and Growth Conditions. All bacterial strains and plasmids used in this study are listed in Table 1. Parental strains 2019, A2 and their derivatives were grown on brain heart infusion agar (Difco) supplemented with 10 µg/ml β-nicotinamide adenine dinucleotide (Sigma) and 10 µg/ml hemin (ICN Biochemicals) at 37° C. When appropriate, 15 µg/ml ribostamycin (Sigma) (a kanamycin analogue), 1 µg/ml chloramphenicol, 15 µg/ml spectinomycin, and 20 µg/ml NeuAc (Sigma) were added to the media.

TABLE 1

| Strains | Genotype | Source or reference |
|---|---|---|
| *E. coli* DH5α | F- f80dlacZDM15 D(lacZYA-argF)U169 deoR recA1 endA1 hsdR17(rK −, mK+) phoA supE44 λ- thi-1 gyrA96 relA1. | Life Technologies |
| *E. coli* DH10B | F- mcrA D(mrr-hsdRMS-mcrBC) f80dlacZDM15 DlacX74 deoR recA1 endA1 araD139 D(ara, leu)7697 galU galK λ- rpsL nupG | Life Technologies |
| *H. influenzae* A2 | Type b strain | Spinola et al., 1990. |
| *H. influenzae* 2019 | Non-Typeable strain | Campagnari et al., 1987. |
| *H. influenzae* A2STF | siaA− | Herein |
| *H. influenzae* A2STFC.P4 | siaA−, plus a functional siaA | Herein |
| *H. influenzae* A2STFIRA | siaA− | Herein |
| *H. influenzae* A2SB | siaB− | Herein |
| H. influenzae 276.4 | lsgE− | Phillips et al., 1996. |
| *H. influenzae* 276.4STF | lsgE−, siaA− | Herein |
| *H. influenzae* A2L3A | lic3A− | Herein |
| *H. influenzae* | siaA−, lic3A− | Herein |

TABLE 1-continued

| | | |
|---|---|---|
| A2STFL3A | | |
| H. influenzae A21sgB | lsgB⁻ | Herein |
| H. influenzae A2STFL3AlsgB | siaA, lic3A⁻, lsgB⁻ | Herein |

| Plasmids | Selection marker and description | Source or reference |
|---|---|---|
| pCR2.1 | Ampicillin, Kanamycin, TA cloning vector | Invitrogen |
| pBluescript KS II⁻ | Ampicillin, cloning vector | Stratagene |
| pHS89-21 | Ampicillin, Kanamycin, siaA cloned into pCR2.1 | Herein |
| pBSL15 | Ampicillin, Kanamycin, used as a backbone for pABR3 and pHiCM1 | Alexeyev, 1995. |
| pBSL86 | Ampicillin, Kanamycin, source of the kanamycin cassette for pHS89-106K6 | Alexeyev, 1995. |
| pABR3 | Ampicillin, Spectinomycin, pBSL15 with a spectinomycin cassette | Alexeyev, 1995. |
| pSiaB2 | Ampicillin, Kanamycin, siaB cloned into pCR2.1 | Herein |
| pSiaB2Spec | Ampicillin, Kanamycin, Spectinomycin, pSiaB2 with a spectinomycin cassette in siaB | Herein |
| pHS89-103 | Ampicillin, siaA from pHS89-21 cloned into pBluescript KS II⁻ | Herein |
| pHS89-103K6 | Ampicillin, Kanamycin, pHS89-103 with a kanamycin cassette in siaA | Herein |
| pTAV1 | Ampicillin, TA cloning vector constructed from pBluescript KS II⁻ | Borovkov et al., 1997. |
| pHiCM1 | Ampicillin, Chloramphenicol, pBSL15 with chloramphenicol cassette | Herein |
| PIRA | Ampicillin, intergenic region from NTHi 2019 cloned into pTAV1 | Herein |
| PIRACM | Ampicillin, Chloramphenicol, pIRA with chloramphenicol cassette | Herein |
| PCMR | Ampicillin, Kanamycin, Chloramphenicol, source of chloramphenicol cassette | Whitby, 1998. |
| p0352EX | Ampicillin, Kanamycin, lic3A gene cloned into pCR2.1 | Herein |
| p0352EXCM | Ampicillin, Kanamycin, Chloramphenicol, p0353EXCM with a chloramphenicol cassette in lic3A | Herein |
| PGEMLOS2 | Ampicillin, lsgA, lsgB, lsgC and lsgD cloned into pGEM3Zf+ | Herein |
| pRSM1775 | Ampicillin, Kanamycin, Chloramphenicol, source of a non-polar chloramphenicol cassette | Herein |
| pGEMLOSABCD | Ampicillin, lsgA, B, C, D cloned into pGEM3zf+ | Herein |
| pGEMLOS2ABCDerm | Ampicillin, Erythromycin, pGEMLOSABCD with an erythromycin cassette in lsgB | Herein |
| pSAIRCM | Ampicillin, Kanamycin, Chloramphenicol, Complementation construct containing the intergenic sequence, chloramphenicol gene, and siaA | Herein |

DNA Isolation and Manipulation. Chromosomal DNA was isolated using standard protocols. Restriction enzymes were purchased from either New England Biolabs or Promega. Polymerase chain reactions (PCR) were performed with either Taq DNA Polymerase (Roche) or the Expand Long Template kit (Roche). All plasmid constructs were maintained in either *Escherichia coli* DH5α or DH10B (Life Technologies). Gel purification was performed with SeaPlaque GTG agarose (BioWittaker Molecular Applications) using standard protocols.

Southern Hybridization. DNA was digested to completion with the appropriate restriction enzymes, fractionated in 0.7% agarose gels and transferred to Hybond-N nylon membranes (Amersham Life Science). Southern blots were hybridized with probes generated by the random primed digoxygenin (DIG) DNA labeling kit (Roche Molecular Biochemicals). All blots were processed by following the DIG protocols. Chemiluminescent detection was performed with Kodak XAR-5 or BMR-1 film (Eastman Kodak Co., Rochester, N.Y.).

DNA Sequencing. DNA was sequenced with the Applied Biosystems automated sequencer using fluorescent terminator dye tags at the DNA Sequencing Facility (University of Iowa). Analysis of the sequence was performed using various programs of the Wisconsin GCG package and the Jellyfish software package developed by Biowire.com. Similarity searches against DNA and protein sequence databases were performed with the FASTA, BLAST or BLASTX algorithms.

Cloning of siaA and Mutant Construction of A2STF. Using the DNA sequence from the *H. ducreyi* lst gene (Bozue et al., 1999), an open reading frame (ORF) in the *H. influenzae* Rd database named HI0871 was identified which contained 48% identity and 59% similarity over the length of the predicted protein sequence. HI0871 was renamed siaA. Primers were made to amplify siaA and some flanking DNA from strain 2019 based on the Rd sequence from the TIGR database. A 4.3 kb product was amplified using the Expand Long Template PCR kit (Roche Molecular Biochemicals) and primers HSTR8 (5'-CTG CAA AAT ACA GAT AAA GCA ACA CTG GGG-3') (SEQ ID NO:5) and HSTR9 (5'-CAG CGG CAA GAA ATA TAG GGT TAG AAA AAG C-3') (SEQ ID NO:6). The 4.3 Kb product was then TA cloned into pCR2.1 (Invitrogen), forming pHS89-21. This insert was then sequenced (GenBank accession no. AY061634). The 4.3 kb DNA fragment was then subcloned into the EcoRI site of pBluescript KS II⁻ (Stratagene), forming pHS89-103.

The insertional mutant of siaA was constructed by cloning a Pst I digested kanamycin antibiotic resistance gene from pBSL86 into a unique Nsi I site in the middle of siaA, forming pHS89-103K6. The orientation of the kanamycin gene was discerned by restriction digest and was found to be transcribed in the same direction as siaA (data not shown). pHS89-103K6 was linearized with ScaI and transformed into strains A2 and 276.4 (Herriott et al., 1970). Transformants were obtained and analyzed using both PCR with internal siaA primers HSTR1 (5'-GAT GTT ATT TTT ATT TTT GTT A-3') (SEQ ID NO:7) and HSTR2 (5'-ACT TAG GGT GTA TTT TGG TTC C-3') (SEQ ID NO:8) and Southern blots (data not shown).

Cloning of siaB and Mutant Construction of A2SB. Primers SiaBU2 (5'-CGG ACT ATC ATA ACG GGC-3') (SEQ ID NO:9) and SiaBD2 (5'-CTC AGA ATT CGG GCT TCG-3') (SEQ ID NO:10) were designed based on the *H. influenzae* Rd genome. A 1.5 kb DNA fragment was amplified from NTHi 2019, TA cloned into pCR2.1, and both DNA strands were sequenced. The new plasmid, called pSiaB2, contained a 675-base pair ORF with 95% identity to HI1279 from *H. influenzae* Rd. pSiaB2 was digested with Ssp I, which cuts at a unique site after nucleotide 276. A spectinomycin resistance cassette gene was digested with Sma I from pABR3 and ligated into the Ssp I site of pSiaB2, forming pSiaB2Spec. pSiaB2Spec was digested with Not I to linearize the DNA and then transformed into strain A2 using the MIV method (Herriott et al., 1970). Transformants were obtained and tested using PCR and Southern hybridization to confirm the proper insertion of the spectinomycin cassette in siaB (data not shown).

Cloning of lsgB and Mutant Construction of A2lsgB and A2STFL3AlsgB. A 3456-bp BamHI-BsbI fragment of *H. influenzae* A2 DNA containing lsgA, -B, -C and -D was cloned into pGEM3zf+. A 502-bp (BsrGI-XcmI) region of lsgB was deleted and replaced by an erythromycin cassette. This new plasmid was called pGEMLOS2ABCDerm, and was digested with NdeI and transformed into strains A2 and A2STFL3A using the MIV method (Herriott et al., 1970). Transformants were obtained and tested using PCR and Southern hybridization to confirm the proper insertion of the erythromycin cassette in lsgB (data not shown). The mutants were designated strains A2lsgB and A2STFL3AlsgB.

TA Cloning of ira from strain 2019. Primers iraF (5'-AGG GGG ATA AAA CAA AGG-3') (SEQ ID NO:11) and iraR (5'-GGC AAG TCC CTG TTC AAA-3') (SEQ ID NO:12) for PCR were designed from the published *H. influenzae* Rd genome. These primers were used to amplify an intergenic region between bases 794506 and 796038. Amplification resulted in a PCR product of approximately 1.6 kb from the genome of NTHi strain 2019. The product was then cloned into the vector pTAV 1 via TA cloning. The nucleotide sequence of the cloned fragment was elucidated and compared to sequences included in the genome database. The resolved consensus sequence was entered into MacVector to identify useful restriction sites. One SphI site was predicted that would cut the cloned region into 711- and 822-base fragments and could be used to linearize pIRA. The presence of the unique SphI site was verified by restriction endonuclease digestion of pIRA.

Construction of pIRA CM. The plasmid pCMR containing a chloramphenicol resistance cassette possessing the consensus uptake sequence for *Haemophilus* transformation was kindly provided by Dr. Terrence Stull (Whitby et al., 1998). To obtain the necessary SphI sites, the chloramphenicol resistance cassette was excised from pCMR using PstI, gel-purified and then ligated into the vector pBSL15 that had been previously cut with PstI. The resulting plasmid was named pHiCM1. Finally, the chloramphenicol resistance cassette was excised from pHiCM1 by cleavage with SphI, gel purified and ligated into the SphI site of pIRA, forming pIRACM. Insertion was confirmed by PCR and by sequencing the cloning junctions.

Complementation of A2STF. A 2.5 kb EcoRV DNA fragment was excised from pHS89-103, gel purified, and blunt end ligated into the SfoI site of pIRACM, forming pSAIRCM. This construct was used as a template for PCR using primers iraR and iraF, and the resulting PCR product was transformed into A2STF using the MIV method (Herriott et al., 1970). Transformants were selected for with both kanamycin and chloramphenicol. Verification that both the full length and the mutant forms of siaA were present on the chromosome was performed with PCR using primers HSTR1 and HSTR2 and with Southern blots (data not shown). A control strain was constructed in a similar fashion by transforming A2STF with pIRA. The insertion into the chromosome was confirmed with Southern blots and the resultant strain was named A2STFIRA (data not shown).

Cloning of lic3A and Mutant Construction of A2L3A and A2STFL3A. Primers 0352ELTU1 (5'-ATG TCC AAA AGC AGC CAA CCA AAT AAA CCC-3') (SEQ ID NO:13) and 0352ELTL1 (5'-CAA CGC CGA AAT CAA CCC AAA TAG AAA GCC-3') (SEQ ID NO:14) were designed using the *H. influenzae* Rd genome database. Using these two primers, a 4.6 kb DNA fragment containing the HI0352 ORF (lic3A) was amplified from strain A2 by PCR. The DNA fragment was TA cloned into pCR2.1, and the resulting construct was named p0352EX. Both DNA strands of p0352EX were sequenced, and a unique SwaI site was found after nucleotide 683 of the 981 nucleotide lic3A sequence. A non-polar chloramphenicol cassette (pRSM 1775), which was constructed in a manner similar to that described by Menard et al. (Menard et al., 1993) using the chloramphenicol gene (cat) from pACYC 184 (Bozue and Munson, Jr., unpublished data), was digested with SmaI and cloned into the SwaI site of lic3A. This construct was named p0352EXCM. The non-polar cassette contains translation stop codons in all three reading frames upstream from the start codon of cat. Five bases after the cat stop codon there is a Shine-Dalgarno sequence followed by a start codon which is in-frame with the remainder of the lic3A gene. The insertion sites of the chloramphenicol cassette were sequenced to insure proper insertion and orientation. p0352EXCM was linearized by digestion with BamHI, and transformed using the MIV method (Herriott et al., 1970) into strains A2 and A2STF, forming strains A2L3A and A2STFL3A, respectively. Proper insertion into the chromosome of these strains was confirmed with PCR amplification, using primers to the lic3A sequence, and Southern hybridization (data not shown).

LOS Preparation and Neuraminidase Treatment. The LOS was prepared by a modification of the Hitchcock and Brown method (Hitchcock and Brown, 1983). Organisms were grown on solid media supplemented with 20 µg/ml of NeuAc. The organisms from a single plate were suspended in 2 ml of phosphate-buffered saline (PBS) buffer to a final $A_{650}$ of 0.9. They were washed twice with PBS, re-suspended in 200 µl of lysis buffer (0.06 M Tris Base, 10 mM EDTA, 2.0% SDS, pH 6.8), and incubated in a boiling water bath for 5-10 minutes. The samples were allowed to cool, and 30 µl of a proteinase K solution (2.5 mg/ml diluted in lysis buffer, Sigma) was added to 150 µl of the boiled sample. The samples were incubated at 37° C. for 16-24 hours. The LOS was precipitated by adding one-tenth volume of 3 M sodium acetate and 2 volumes of 100% ethanol, put on dry ice for 10 minutes or in a −80° C. freezer for 1 hour, and then centrifuged at 15,000×g for 5 minutes. The samples were washed twice with 70% ethanol and brought up in double-distilled (dd)$H_2O$ to a final volume of 180 µl. For SDS-PAGE gel analysis, 1-5 µl (approximately 0.5 to 2.5 µg of LOS) of a typical preparation was treated with 0.5 milliunits of neuraminidase purified from *Vibrio cholerae* (Roche Molecular Biochemicals) in neuraminidase buffer (0.15 M NaCl, 4 mM $CaCl_2$, pH 5.5) and incubated at 37° C. for 2 hours.

SDS-PAGE, Silver Staining, and Western Blotting. SDS-PAGE gels were prepared as described by Lesse et al. (Lesse et al., 1990). The gel was loaded with 0.5 to 1 µl from each LOS preparation (approximately 0.25 to 0.5 µg of LOS. Silver staining was performed by the method of Tsai and Frasch (Tsai and Frasch, 1982). The Western blot was performed by the method of Towbin (Towbin et al., 1979). The monoclonal antibody 3F11 recognizes a terminal N-acetyllactosamine structure and has been characterized previously (Yamasaki et al., 1991). Detection of the antibody was performed using a peroxidase labeled goat anti-mouse secondary antibody (Kirkegaard and Perry Laboratories) and Super Signal West Pico Chemiluminescent Substrate (Pierce). LOS from *N. gonorrhoeae* strain PID2 was used as a molecular weight standard (Schneider et al., 1991).

Whole Cell 3F11 ELISA. A whole-cell enzyme-linked immunosorbent assay (ELISA) was performed using the monoclonal antibody 3F11 and a modified method of Abdillahi and Poolman (Abdillahi and Poolman, 1987). Whole bacteria were harvested from plates containing 20 µg/ml of NeuAc (Sigma), suspended in PBS and washed twice. The cell suspensions were diluted with dd$H_2O$ to an $A_{600}$ of 0.150. 100 µl of the cell suspension was added to the wells of flat bottom high binding polystyrene 96 well plates (Costar) and allowed to dry completely at 37° C. Unbound material was removed by rinsing the plates with wash buffer (0.12 M sodium acetate, 0.15 M NaCl, 0.05% Tween 20). Half of the wells were treated with neuraminidase from *Vibrio cholerae* (Roche Molecular Biochemicals) in neuraminidase buffer (0.15 M NaCl, 4 mM $CaCl_2$, pH 5.5), and the other half were incubated in neuraminidase buffer alone for 6 hours at 37° C. in a humidified chamber. The plates were washed again, and 100 µl of the monoclonal antibody 3F11 in antibody buffer (0.15 M NaCl, 10 mM Tris pH 7.4, 0.3% Tween 20) was serially diluted two-fold from a starting dilution of 1:40. The plates were incubated at 25° C. overnight. The plates were washed, and 100 µl of a 1:2000 dilution of goat anti-mouse IgM phosphatase-conjugated secondary antibody (Kirkegaard and Perry Laboratories) was added to each well and allowed to incubate at 25° C. for 1 hour. The plates were washed and 100 µl of developer (1 mg/ml p-nitrophenyl phosphate, (Sigma) 0.96% diethanolamine, 2 mM $MgCl_2$, pH 10.0) was added to each well. The samples were allowed to develop for 30 minutes and 50 µl of 4 N NaOH was added to each well to quench the reaction. The plates were read at 405 nm with a Bio-Tec Instruments EL 311SX microplate reader.

Preparation of O-deacylated Lipooligosaccharides (O-LOS) and Neuraminidase Treatment. To make the LOS more amenable for mass spectrometric analysis, O-linked fatty acids were removed from the lipid A moiety. The crude LOS (approximately 90 µg, from a single plate) was incubated in anhydrous hydrazine (50 µl, Sigma) at 37° C. for 25 minutes in a microcentrifuge tube, with occasional sonication. Samples were cooled at −10° C. for 10 minutes prior to and after the addition of ice cold acetone (300 µl, Aldrich). The quenched reaction mixture was centrifuged (12,000×g) for 45 minutes at 4° C. The supernatant was removed and the pelleted O-LOS was dissolved in MilliQ water (40 µl) and evaporated on a speed vacuum system. To remove salts and other low molecular weight contaminants, the O-LOS (approximately 10-20 µg) was suspended on a nitrocellulose membrane (type VS, 0.025 µm, Millipore Corp.) over water for 1 hour. The desalted O-LOS was removed from the membrane, concentrated with a speed vacuum system and analyzed by matrix-assisted laser desorption ionization-mass spectrometry (MALDI-MS). For removal of neuraminic acid, the O-LOS (approximately 10-20 µg) was digested in 10 mM ammonium acetate, pH 6.0 with immobilized neuraminidase from *Clostridium perfringens* (type VI, 80 milliunits) for 20 hours at 30° C. The enzyme was pelleted by centrifugation, and the supernatant (15 µl) was transferred to a nitrocellulose membrane for drop dialysis. The de-sialylated O-LOS was also concentrated and analyzed by MALDI-MS.

Matrix Assisted Laser Desorption Ionization-Mass Spectrometry (MALDI-MS) of O-LOS. Dowex 50 beads (100-200 mesh, $NH_4^+$ form) were added to a mixture containing equal volumes of dialyzed O-LOS (approximately 2 µg/µl) and a saturated solution of 2,5-dihydroxybenzoic acid in acetone (Aldrich). Samples were spotted on a stainless steel MALDI target and analyzed on a Voyager-DE time of flight mass spectrometer (Applied Biosystems) in the negative ion mode with an accelerating voltage of 20 kV. Mass spectra were smoothed once by a 19 point Savitsky-Golay function and calibrated internally with the deprotonated molecular ions corresponding to LOS glycoforms $A_1$ (m/z=2438.1), $A_2$ (m/z=2561.2), $B_1$ (m/z=2600.3), $B_2$ (m/z=2723.3), $C_1$ (m/z=2762.4), $C_2$ (m/z=2885.5) (see Table 2) and the prompt fragment for lipid A (m/z=952.0). All masses are given as their average values.

TABLE 2

Summary of asialo-LOS glycoforms present in the wild type and mutant strains of *H. influenzae* A2.

| Glycoform | Compositions | | | Calculated |
|---|---|---|---|---|
| $X_{PEA}$ | HexNAc | Hex | PEA | $[M - H]^-$ |
| Hexose Containing Structures | | | | |
| $A_1$ | 3 | 1 | | 2438.1 |
| $A_2$ | 3 | 2 | | 2561.2 |
| $B_1$ | 4 | 1 | | 2600.3 |
| $B_2$ | 4 | 2 | | 2723.3 |
| $C_1$ | 5 | 1 | | 2762.4 |
| $C_2$ | 5 | 2 | | 2885.5 |
| $D_1$ | 6 | 1 | | 2924.6 |

TABLE 2-continued

Summary of asialo-LOS glycoforms present in the wild type and mutant strains of *H. influenzae* A2.

| Glycoform | Compositions | | | Calculated |
|---|---|---|---|---|
| $X_{PEA}$ | HexNAc | Hex | PEA | $[M - H]^-$ |
| $D_2$ | | 6 | 2 | 3047.6 |
| $E_1$ | | 7 | 1 | 3086.7 |
| $E_2$ | | 7 | 2 | 3209.8 |
| $F_1$ | | 8 | 1 | 3248.9 |
| $F_2$ | | 8 | 2 | 3371.9 |
| N-Acetylhexosamine Containing Structures | | | | |
| $G_1$ | 1 | 5 | 1 | 2965.6 |
| $G_2$ | 1 | 5 | 2 | 3088.7 |
| $H_1$ | 1 | 6 | 1 | 3127.8 |
| $H_2$ | 1 | 6 | 2 | 3250.8 |
| $I_1$ | 1 | 7 | 1 | 3289.9 |
| $I_2$ | 1 | 7 | 2 | 3413.0 |
| Extended Structures Found in siaA Mutants | | | | |
| $J_2$ | 2 | 5 | 2 | 3291.9 |
| $J_3$ | 2 | 5 | 3 | 3414.9 |
| $K_2$ | 2 | 6 | 2 | 3454.0 |
| $K_3$ | 2 | 6 | 3 | 3577.0 |
| $L_2$ | 2 | 7 | 2 | 3616.1 |
| $L_3$ | 2 | 7 | 3 | 3739.2 |

Proposed compositions contain a minimum core structure including $Hep_3$, Kdo(P), O-deacylated Lipid A. PEA moieties are denoted by subscripts. All masses listed are average values.

Exoglycosidase treatments of O-LOS. To sequence non-reducing terminal saccharides, O-LOS samples were treated with exoglycosidases. The following enzymes were used in these experiments: α-galactosidase from *Mortierella vinacea* (Seikagaku Corp.) or from green coffee beans (Glyko, Inc.), β-galactosidase from jack bean meal (Glyko, Inc.), β-N-acetylhexosaminidase from jack bean meal (Glyko, Inc.), α-N-acetylgalactosaminidase from chicken liver (Sigma), α-glucosidase from *Bacillus stearothemophilus* (Sigma), β-glucosidase from almonds (Sigma), and immobilized neuraminidase from *Clostridium perfringens*, type VI (Sigma). In general, enzyme reactions were run in 25-50 mM ammonium acetate buffer, at pH 4.5 or pH 6.0, depending on the enzyme (pH 4.5 for the three enzyme mixture consisting of α-galactosidase, β-galactosidase, and β-N-acetylhexosaminidase). The immobilized neuraminidase was used as described above, except that in these experiments the incubation temperature was 37° C. Soluble enzyme concentrations were typically in the range of 5-10 units/ml, and total O-LOS concentrations were estimated to be in the range of approximately 100-200 μM. For the 276.4STF sample, the minor acceptor glycoform of interest was estimated to represent ≦1% of the total O-LOS mixture, making its concentration in the enzyme digest reactions on the order of approximately 1-2 μM.

Various sequences of enzyme digests were carried out, generally starting with the O-LOS from 1-1.5 plates' worth of bacteria, in a reaction volume of 60-90 μl. Digests were incubated at 37° C. for 20-24 hours. Except in the case of the immobilized neuraminidase, reactions were stopped by heating in a boiling water bath for 3 minutes. After quenching, reaction mixtures were typically delivered to prewashed Microcon YM-10 filter units (Millipore) and spun at 10,000×g for 5-15 minutes, depending on the reaction volumes. Samples were then washed with several 50-100 μl aliquots of MilliQ water, totaling about 400 μl. Retentates were recovered by inverting the filters and centrifuging at low speed. Filters were washed with three portions of 20-40 μl of MilliQ water, and the washings were combined with the retentates and evaporated to dryness on a speed vacuum system. Because of its tendency to aggregate in solution, the O-LOS was recovered in the retentate fraction using these membrane filters. Samples were then redissolved in MilliQ water for MALDI MS analysis as described above.

Dephosphorylation of O-LOS. O-LOS samples were dephosphorylated by treatment with 48% aqueous HF for 16 hours at 4° C. HF was removed under vacuum using an in-line NaOH trap. Samples were then redissolved in a small volume of MilliQ water and evaporated to dryness on a speed vacuum system.

Results

Cloning and mutagenesis of siaA. The ORF HI0871 from the *H. influenzae* Rd genome database encodes a predicted protein of 306 amino acids. This protein sequence has 48% identity and 59% similarity along the entire length of the recently identified Lst protein from *H. ducreyi* (Bozue et al., 1999). Lst is the sialyltransferase responsible for the addition of NeuAc to galactose of a terminal N-acetyllactosamine moiety of the LOS (Bozue et al., 1999). Based on the Rd sequence, primers were made to amplify the HI0871 ORF and about 1.5 kb of flanking sequence on either side of the ORF. The primers were able to amplify a DNA fragment of similar expected size from strains Rd, 2019, and A2. The DNA fragment from strain 2019 was sequenced in its entirety and the gene order was found to be similar, but not identical to the Rd sequence. The DNA fragment contained the 3' partial sequence of HI0868, the full length HI0871 (renamed siaA) and the 5' partial sequence of HI0872 (wbaP homologue, formerly rfbP). There was 46% identity and 57% similarity between the predicted proteins of Lst from *H. ducreyi* and SiaA from NTHi 2019, and 58% identity and 70% similarity between the predicted proteins of SiaA from NTHi 2019 and HI0871. There is a five base overlap at the 3' end of siaA and the 5' end of wbaP. HI0869 contained an insertion after position 533 causing a frame shift resulting in an extension of the ORF. In addition to this, there was a small ORF (ORF1) upstream of siaA that was not present in the Rd sequence. Both HI0869 and ORF1 do not have any identity to any known genes in the current databases.

An insertional mutation was made in siaA of strains A2 and 276.4 by inserting a kanamycin cassette from pBSL86 into a NsiI site in the middle of the gene. This construct was called pHS89-103K6. Restriction digest analysis demonstrated that the kanamycin cassette, which does not contain a transcriptional termination sequence, was inserted in the same orientation as siaA. The transformation of strains A2 and 276.4 with pHS89-103K6 employing the MIV method (Herriott et al., 1970) yielded numerous transformants. The mutant strains from A2 and 276.4 were named A2STF and 276.4STF, respectively. PCR analysis using probes that amplify an intergenic region of siaA, along with Southern hybridization, confirmed the single insertion of the kanamycin cassette in siaA of both strains A2STF and 276.4STF.

Identification of LOS Glycoforms in *H. influenzae* A2. Prior to investigating the effects of inactivating genes responsible for LOS biosynthesis in *H. influenzae*, the population of glycoforms assembled by stain A2 was assessed with MALDI-MS in the negative ion mode. All observed molecular ions and the proposed LOS compositions for structures containing a minimum core structure of lipid A linked to a phosphorylated Kdo and three heptoses are summarized in Table 2. Letters represent individual glycoforms to which NeuAc (each denoted by an asterisk)

and one to three PEAs (denoted by subscripts) are added. MALDI-MS analysis of the O-LOS revealed that the A2 strain expresses an even more complex mixture of glycoforms on its outer membrane than previously thought (Phillips et al., 1996). Most structures represented extensions of the major species ($B_1$ and $B_2$) by up to four additional hexoses (FIG. 1, Table 3).

TABLE 3

Summary of sialylated LOS glycoforms in *H. influenzae* A2, A2STF and A2STFC.P4.

| Glycoform $X_{PEA}$ | Calculated $[M - H]^-$ | A2 $[M - H]^-$ | A2STF $[M - H]^-$ | A2STFC.P4 $[M - H]^-$ |
|---|---|---|---|---|
| Hexose-containing structures | | | | |
| $B_2*$ | 3014.6 | 3014.0 | 3014.6 | 3014.5 |
| $D_2*$ | 3338.9 | 3338.4 | 3339.0 | |
| $E_2*$ | 3501.0 | 3500.4 | 3501.1 | 3501.4 |
| N-Acetyllactosamine containing structures | | | | |
| $H_1*$ | 3419.0 | 3418.7 | | |
| $H_2*$ | 3542.1 | 3541.2 | 3540.7 | 3541.9 |
| $H_2**$ | 3833.3 | 3832.7 | | 3833.4 |
| $I_1*$ | 3581.2 | 3580.8 | 3582.6 | 3580.1 |
| $I_2*$ | 3704.2 | 3705.2 | | 3705.0 |
| Extended structures found in siaA mutant | | | | |
| $K_2*$ | 3745.3 | | 3742.7 | |
| $K_3*$ | 3868.3 | | 3868.4 | |
| $K_3**$ | 4159.6 | | 4159.8 | |
| $L_2*$ | 3907.4 | | 3905.1 | |
| $L_3*$ | 4030.4 | | 4030.8 | |

Refer to Table 2 for glycoform compositions. The number of NeuAc and PEA moieties are denoted by asterisks and subscripts, respectively. All masses listed are average values.

An examination of the O-LOS proceeding the enzymatic removal of NeuAc with neuraminidase confirmed the removal of a total of eight sialylated glycoforms which coincided with the appearance of the asialo counterparts (FIG. 1, Table 3). In general, the most abundant structures terminating with NeuAc contained a single N-acetylhexosamine and a total of six or seven hexoses ($H_1*$, $H_2*$, $I_1*$, and $I_2*$). Tandem mass spectrometric analysis of the oligosaccharide portions of the H and I glycoforms revealed the structures contained a nonreducing terminal Hex-Hex-NAc (consistent with a N-acetyllactosamine structure), the putative acceptor site for NeuAc (Samuels and Gibson, unpublished data). Interestingly, previous investigations of the A2 strain by electrospray mass spectrometry revealed only two sialylated LOS glycoforms, each comprised of a single N-acetylhexosamine and a total of five or six hexoses. This discrepancy presumably reflects the altered growth conditions as the bacteria were grown on solid media supplemented with NeuAc in the current study (Phillips et al., 1993). Furthermore, several novel sialylated species were observed including a structure containing two NeuAcs ($H_2**$) and three structures lacking N-acetylhexosamine ($B_2*$, $D_2*$, and $E_{2*}$). The $H_2**$ glycoform was found to be resistant to enzymatic digestion with a mixture of α-galactosidase, β-galactosidase, and β-N-acetylhexosaminidase, suggesting that it may be sialylated on two different branches (Phillips, Gibson and Apicillen, unpublished data).

Analysis of LOS from A2STF. MALDI-MS analysis of the LOS from the siaA mutant strain (A2STF) revealed no gross changes in the expression of LOS whose branch structures contain only hexose relative to those observed in the parental strain A2 (FIG. 1, Table 3). However, the deletion of siaA impaired the ability of the mutant strain to produce the major sialylated species ($H_1*$, $H_2*$, $H_2**$, $I_1*$, and $I_2*$), leaving the putative LOS substrates of SiaA ($H_1$, $H_2$, $I_1$, and $I_2$) unmodified. The A2STF mutant strain retained the capacity to produce the previously identified sialylated species ($B_2*$, $D_2*$, and $E_2*$), as well as additional structures containing both NeuAc and N-acetylhexosamine ($K_2*$, $K_3*$, $K_3**$, $L_2*$, and $L_3*$) that were not observed in the parental strain A2 (FIG. 1, Table 3). The emergence of the unique set of glycoforms in strain A2STF coincided with the extension of the free SiaA acceptors ($H_1$, $H_2$, $I_1$, and $I_2$) by the addition of an approximately 617 Da moiety, suggesting the addition of HexNAc (203 Da), PEA (123 Da), and NeuAc (291 Da) (discussed below). The expression of these and other sialylated LOS structures upon the mutation of siaA provided strong evidence that multiple sialyltransferases of distinct substrate specificity reside on the outer membrane of *H. influenzae* strain A2.

Complementation of A2STF. To verify that the changes in the LOS glycoforms observed in A2STF were the result of a mutation in siaA, the mutation was complemented in cis. This was accomplished using the construct pSAIRCM, which was made from a 1.5-kb intergenic region identified in the Rd database and found to be present in the chromosome of strain A2 by PCR analysis. pSAIRCM was transformed into A2STF using the MIV method (Herriott et al., 1970). A homologous recombination event at the intergenic region resulted in the incorporation of both the chloramphenicol cassette and full-length siaA genes into that region of the chromosome. Transformants were selected with both kanamycin and chloramphenicol to avoid the loss of the original insertional mutant in siaA. This strain was named A2STFC.P4.

A control strain was constructed to verify that the effects seen in the complemented mutant were not due to the insertion of the chloramphenicol cassette into the intergenic region. Strain A2STFIRA was constructed in an identical manner to A2STFC.P4, with the exception that pIRACM was used instead of pSAIRCM. The insertion of the chloramphenicol cassette into the intergenic region was confirmed with Southern hybridization. There were no differences in either the growth curves or the MALDI-MS spectra when strain A2STF was compared to strain A2STFIRA. Complementation of the siaA mutation was verified by MALDI-MS analysis of LOS assembled by the A2STFC.P4 mutant strain (FIG. 1, Table 3). Reversion to the wild type phenotype was evident by the reappearance of both the minor and major sets of sialylated glycoforms detected in the parental strain.

Analysis of 276.4 and 276.4STF. The mutation in strain 276.4 has been characterized previously (Phillips et al., 1996). The mutation lies in lsgE, one of the seven genes in the lsg locus of *H. influenzae* (Spinola, 1990; Phillips et al., 2000). SDS-PAGE revealed that the inactivation of lsgE results in the expression of three major glycoforms of approximately 4.2, 4.4, and 5.4 kDa, a much simpler profile when compared to the parental strain A2 (data not shown). The 5.4-kDa glycoform is of particular interest to this study because it contains a terminal sialyl N-acetyllactosamine structure (Phillips et al., 1996). SDS-PAGE analysis also revealed that the disappearance of the 5.4 kDa glycoform following neuramindase treatment coincides with the appearance of a band of approximately 5.1 kDa, a 300-kDa shift corresponding to the loss of a single NeuAc residue (data not shown).

The LOS was transferred to a nylon membrane and probed with the monoclonal antibody 3F11, which recognizes the terminal N-acetyllactosamine structure. If NeuAc or other sugars are present extending from this epitope, the binding of 3F11 is blocked. Western blot analysis demonstrated that 3F11 was able to bind LOS from strain 276.4 only after neuraminidase treatment (data not shown). The binding corresponded to the 5.1-kDa glycoform. 3F11 binding to the 276.4 LOS before neuraminidase treatment could not be demonstrated by Western blotting, even after the blot was overexposed (data not shown).

An insertional mutant in the siaA gene in strain 276.4 was constructed.

Strain 276.4 was transformed using the MIV method (Herriott et al., 1970) with pHS89-103K6 and transformants were obtained. Verification of the proper insertion of the kanamycin cassette in the siaA gene was confirmed with PCR and Southern hybridization analysis. The resulting strain was named 276.4STF. The LOS profile from 276.4STF contained four major glycoforms of approximately 4.2, 4.4, 5.1, and a new glycoform of approximately 5.8 kDa. Both of the 5.1- and 5.8-kDa glycoforms were minor species and appear as faint bands when visualized with SDS-PAGE (data not shown). When this sample was treated with neuraminidase, the 5.8 kDa glycoform shifted to approximately 5.4 kDa, indicating the loss of NeuAc. When the LOS was transferred to a nylon membrane and probed with 3F11, the antibody bound to the 5.1-kDa glycoform in the neuraminidase treated 276.4STF LOS sample, but with less intensity as the neuraminidase treated 276.4 LOS sample (data not shown). After overexposure of the blot, 3F11 was also visualized binding to the 276.4STF LOS sample before neuraminidase treatment (data not shown). There was no antibody binding observed to the LOS of strain 276.4STF in the 5.4-kDa size range, even after the blot was overexposed (data not shown). These data indicated that although the 5.8-kDa glycoform contained NeuAc, it lacked a terminal N-acetyllactosamine structure. MALDI-MS analysis of these samples confirmed these results (discussed below).

Mutant construction and MALDI analysis of lic3A in strains A2 and A2STF. The higher molecular weight sialylated species seen in both A2STF and 276.4STF indicated the possibility of a second sialyltransferase in this organism. Analysis suggested that this second sialyltransferase would have a different specificity than a terminal N-acetyllactosamine structure. This was based on the fact that Western blot analysis with 3F11 indicated this terminal structure was lost in the 276.4STF mutant, but sialylation was retained. Recently a sialyltransferase was reported in a *H. influenzae* gene called lic3A, which is the first gene in the lic3 locus (Maskell et al., 1991; Hood et al., 2001). This gene is phase-variable and its protein product sialylates both lactose and N-acetyllactosamine in vitro, but only lactose containing structures in vivo (Hood et al., 2001). Lic3A has around 40% identity to CstII from *C. jejuni* (Hood et al., 2001). This protein in *C. jejuni* is a bifunctional sialyltransferase, with the ability to transfer NeuAc to terminal galactose residues as well as the O-8 position of terminal NeuAcs (Gilbert et al., 2000). To investigate the possibility of Lic3A being the sialyltransferase responsible for sialylating the higher molecular weight species of A2STF, a mutation in lic3A was made in both strains A2 and A2STF. Primers were made to the DNA sequence upstream and downstream of HI0352, the lic3A homologue in Rd, based on the published *H. influenzae* Rd genomic sequence. A DNA fragment was PCR amplified from strain A2 that was similar in size to the expected Rd fragment. This fragment was TA cloned, forming plasmid p0352EX. Both strands of the amplified DNA of p0352EX were sequenced and compared to the known sequences in the database. The gene order in p0352EX was identical to that in Rd. Downstream from lic3A was the galE homologue HI0351, and the 5' portion of HI0350, a hypothetical membrane protein. Upstream from the lic3A gene was HI0354 and the 5' portion of HI0355. A non-polar chloramphenicol cassette was inserted in the middle of lic3A, forming p0352EXCM. This construct was linearized and transformed into strains A2 and A2STF. Transformants from the A2 and A2STF transformation were named A2L3A and A2STFL3A, respectively. Proper insertion of the chloramphenicol cassette was confirmed with Southern hybridization (data not shown).

Figure 2:
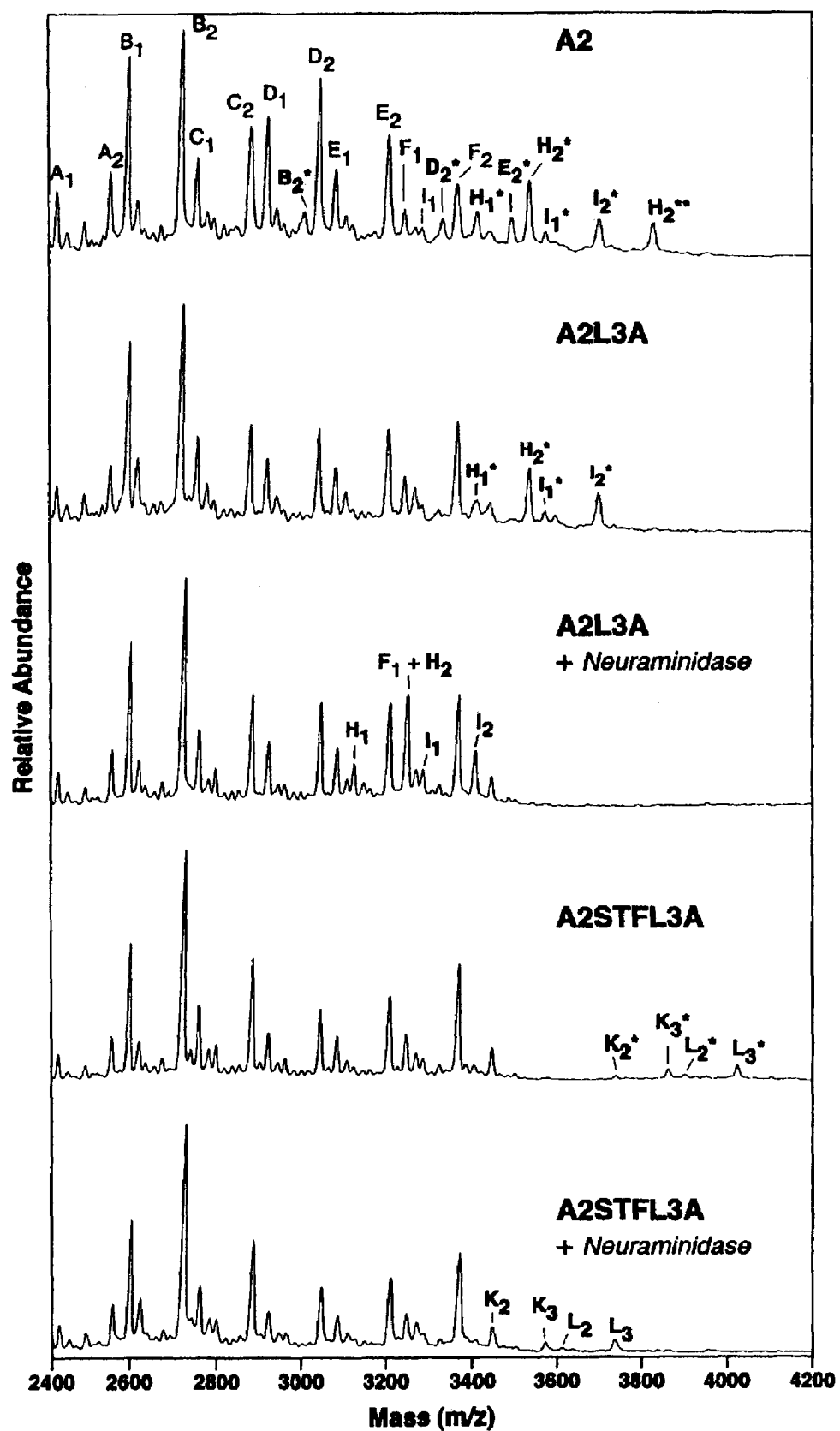
FIG. 2 depicts negative ion MALDI-MS spectra of O-LOS from *H. influenzae* A2, A2L3A, and A2STFL3A. Mass spectra are shown comparing LOS isolated from *H. influenzae* strains before and after treatment with neuraminidase. See Tables 2 and 4 for molecular weights and compositions. The asterisks indicate the addition of NeuAc, and the number of PEA moieties is denoted by subscript.

MALDI-TOF analysis of the LOS expressed by strain A2L3A revealed the loss of both the disialylated ($H_2$**) and hexose containing ($B_2$*, $D_2$*, and $E_2$*) species, but confirmed the presence of the major sialylated species ($H_1$*, $H_2$*, $I_1$*, and $H_2$*) observed in the parental strain A2 (FIG. 2, Table 4).

TABLE 4

Summary of sialylated LOS glycoforms in
*H. influenzae* A2, A2L3A and A2STFL3A.

| Glycoform $X_{PEA}$ | Calculated $[M - H]^-$ | A2 $[M - H]^-$ | A2L3A $[M - H]^-$ | A2STFL3A $[M - H]^-$ |
|---|---|---|---|---|
| Hexose Containing Structures | | | | |
| $B_2$* | 3014.6 | 3014.0 | | |
| $D_2$* | 3338.9 | 3338.4 | | |
| $E_2$* | 3501.0 | 3500.4 | | |
| N-Acetyllactosamine Containing Structures | | | | |
| $H_1$* | 3419.0 | 3418.7 | 3417.0 | |
| $H_2$* | 3542.1 | 3541.2 | 3541.9 | |
| $H_2$** | 3833.3 | 3832.7 | | |
| $I_1$* | 3581.2 | 3580.8 | 3579.9 | |
| $I_2$* | 3704.2 | 3705.2 | 3703.9 | |
| Extended Structures Found in siaA Mutant | | | | |
| $K_2$* | 3745.3 | | | 3744.3 |
| $K_3$* | 3868.3 | | | 3867.8 |
| $L_2$* | 3907.4 | | | 3906.9 |
| $L_3$* | 4030.4 | | | 4030.1 |

Refer to Table 2 for glycoform compositions. The number of NeuAc and PEA moieties are denoted by asterisks and subscripts, respectively. All masses listed are average values.

This indicated that in strain A2, the Lic3A homologue has substrate specificity distinct from SiaA, preferring to transfer NeuAc to LOS glycoforms devoid of N-acetylhexosamine. The loss of the disialylated glycoform $H_2$** may reflect the inability of the A2L3A mutant to sialylate one branch of the $H_2$ structure. The mass spectra of the LOS isolated from strain A2STFL3A revealed the double mutant lost the ability to produce the SiaA products ($H_1$*, $H_2$* $I_1$*, and $H_2$*) containing N-acetylhexosamine (FIG. 2, Table 4). Strain A2STFL3A did produce sialylated species ($K_2$*, $K_3$*, $L_2$*, and $L_3$*) that were not previously observed in either strain A2L3A or the parental strain A2, but were identified in strain A2STF. Since the deletion of both siaA and lic3A precludes the assembly of only certain subsets of NeuAc containing LOS glycoforms of *H. influenzae* strain A2, their gene products function as sialyltransferases. Thus, the existence of a third sialyltransferase in this complex system has been demonstrated.

Exoglycosidase treatments of 276.4STF O-LOS. To investigate the structures of the extended glycoforms produced in the siaA mutants, experiments were conducted on the O-LOS from strain 276.4STF. The sialylated acceptor species in 276.4STF, designated J$_3$*, is a minor component in the O-LOS mixture occurring at m/z approximately 3706 Da (Table 5).

TABLE 5

Summary of LOS glycoforms in *H. influenzae* 276.4 and 276.4STF.

| Glycoform X$_{PEA}$ | Calculated [M − H]$^−$ | 276.4 [M − H]$^−$ | 276.4STF [M − H]$^−$ |
|---|---|---|---|
| Hexose Containing Structures | | | |
| (A$_1$-Hex) | 2276.0 | 2275.8 | 2275.7 |
| (A$_2$-Hex) | 2399.0 | 2398.8 | 2398.8 |
| A$_1$ | 2438.1 | 2438.0 | 2438.0 |
| A$_2$ | 2561.2 | 2561.0 | 2561.0 |
| B$_1$ | 2600.3 | 2600.1 | 2600.1 |
| B$_2$ | 2723.3 | 2723.3 | 2723.3 |
| N-Acetylhexosamine Containing Structures | | | |
| G$_2$ | 3088.7 | 3089.1 | 3088.2 |
| G$_1$* | 3256.9 | 3256.6 | |
| G$_2$* | 3379.9 | 3379.8 | 3379.1 |
| Extended Structures Found in siaA Mutant | | | |
| J$_2$* | 3583.1 | | 3582.7 |
| J$_3$* | 3706.2 | | 3705.8 |

Refer to Table 2 for glycoform compositions. The number of NeuAc and PEA moieties are denoted by asterisks and subscripts, respectively. All masses listed are average values.

Compared to the sialylated G$_2$* glycoform in O-LOS from strain 276.4 (Table 5), this species was approximately 324-326 Da higher in molecular weight. Initially, it was assumed that the added moiety was a Hex$_2$ extension, which would have corresponded to the same composition as the A2 wild-type I$_2$* glycoform. However, dephosphorylation of the O-LOS sample with aqueous HF revealed that the novel acceptor species contained three PEAs, rather than the one or two PEAs present on all of the major components in the mixture. This observation indicated that the added structural pieces had to be HexNAc plus PEA (+326 Da), rather than Hex$_2$ (+324 Da).

To sequence the terminus of the J$_3$* species, the O-LOS from strain 276.4STF was subjected to a series of exoglycosidase treatments and analyzed by MALDI-MS (data not shown). As a first step, the sample was treated with a mixture of three enzymes consisting of α-galactosidase, β-galactosidase, and β-N-acetylhexosaminidase. This treatment was done to insure that any nonreducing terminal saccharides of this type that were not blocked by sialylation would be removed from the species before sequencing of the acceptor began. In the case of strain 276.4STF, the mixture treatment did not alter the glycoform profile of the sample except to remove a small peak for the G$_2$ species. However, when strain A2STFL3A O-LOS was subjected to the mixture treatment, various high molecular weight glycoforms were digested with the enzymes, such that the final profile of the strain A2STFL3A O-LOS population was virtually identical to the strain 276.4STF O-LOS profile, except for minor differences in the PEA content of the species. The high molecular weight sialylated glycoforms in the strain A2STFL3A sample (the K$_2$*/K$_3$* and L$_2$*/L$_3$* glycoforms given in Table 4) were converted to the J$_2$*/J$_3$* species by the loss of 1 and 2 galactoses, respectively. This indicated that the J$_3$* species contained the essential structure of the novel acceptor branch found in the O-LOS from both the A2STFL3A and 276.4STF strains.

After the mixture treatment, the strain 276.4STF sample was neuraminidase-treated and then tested with a battery of exoglycosidases. Using this approach, none of the following enzymes were effective at removing a terminal sugar from the asialo acceptor: α-galactosidase, β-galactosidase, α-glucosidase, β-glucosidase, β-N-acetylhexosaminidase, and α-N-acetylgalactosaminidase.

As an alternate approach, the mixture-treated strain 276.4STF sample was subjected to dephosphorylation with aqueous HF prior to further enzymatic treatments. To minimize the loss of sialic acid in the dephosphorylation step, the reaction time was kept to ≦16 hours. Under these conditions, microheterogeneity was created in the sample, with asialo and sialylated species appearing as pairs containing 0 or 1 residual phosphate group. When the HF-treated strain 276.4STF sample was subjected to α-N-acetylgalactosaminidase treatment, all of the asialo and sialylated glycoforms of the acceptor were shifted to lower mass by the loss of 203 Da, indicating the removal of an α-linked N-acetylgalactosamine (α-GalNAc). At this point, the sample was split into two portions, one treated with β-galactosidase and one treated with neuraminidase followed by β-galactosidase. In the sample treated first with β-galactosidase, only the asialo glycoform was shifted, indicating the removal of β-linked galactose. The sialylated glycoform was shifted to the same species in a sequential fashion by neuraminidase treatment (−291 Da) followed by β-galactosidase treatment (−162 Da).

Cloning and mutagenesis of lsgB. The lsgB has been previously described in the lsg locus of *Haemophilus influenzae* as orf 2 (GenBank accession no. Q48211) and in the TIGR *H. influenzae* Rd database as ORF HI1699. It encodes a predicted protein of 304 amino acids. This protein sequence has 27% identity and 46% similarity along the entire length of the recently identified α2-3sialyltransferase (Lst) protein from *N. gonorrhoeae* and *N. meningitidis* (Phillips et al., 2000; Bozgue et al., 1999). Lst is the sialyltransferase responsible for the addition of NeuAc to galactose of a terminal N-acetyllactosamine moiety of the LOS. To clone this gene for mutagenesis and transformation, a Bbs I-Pst I digest of the lsg locus in the plasmid pGEM-LOS4 released a 2161 bp fragment. The plasmid was re-ligated containing lsgA (lsg orf1), lsgB (lsg orf2) and lsgC (lsg orf3) and part of lsgD (lsg orf4). Using this construct, a deletion mutant was made in lsgB by deleting 506 bases with a BsrGI-XcmI digest of this fragment and inserting an erythromycin cassette. This cassette was placed in the forward orientation and does not contain a transcriptional termination sequence. The plasmid was linearized and transformed into strains A2 and A2STFL3A by the MIV method using appropriate selection. The resulting strains were designated A2lsgB and A2STFL3AlsgB. The chromosomal insertions were confirmed by PCR and Southern hybridization.

Figure 3:
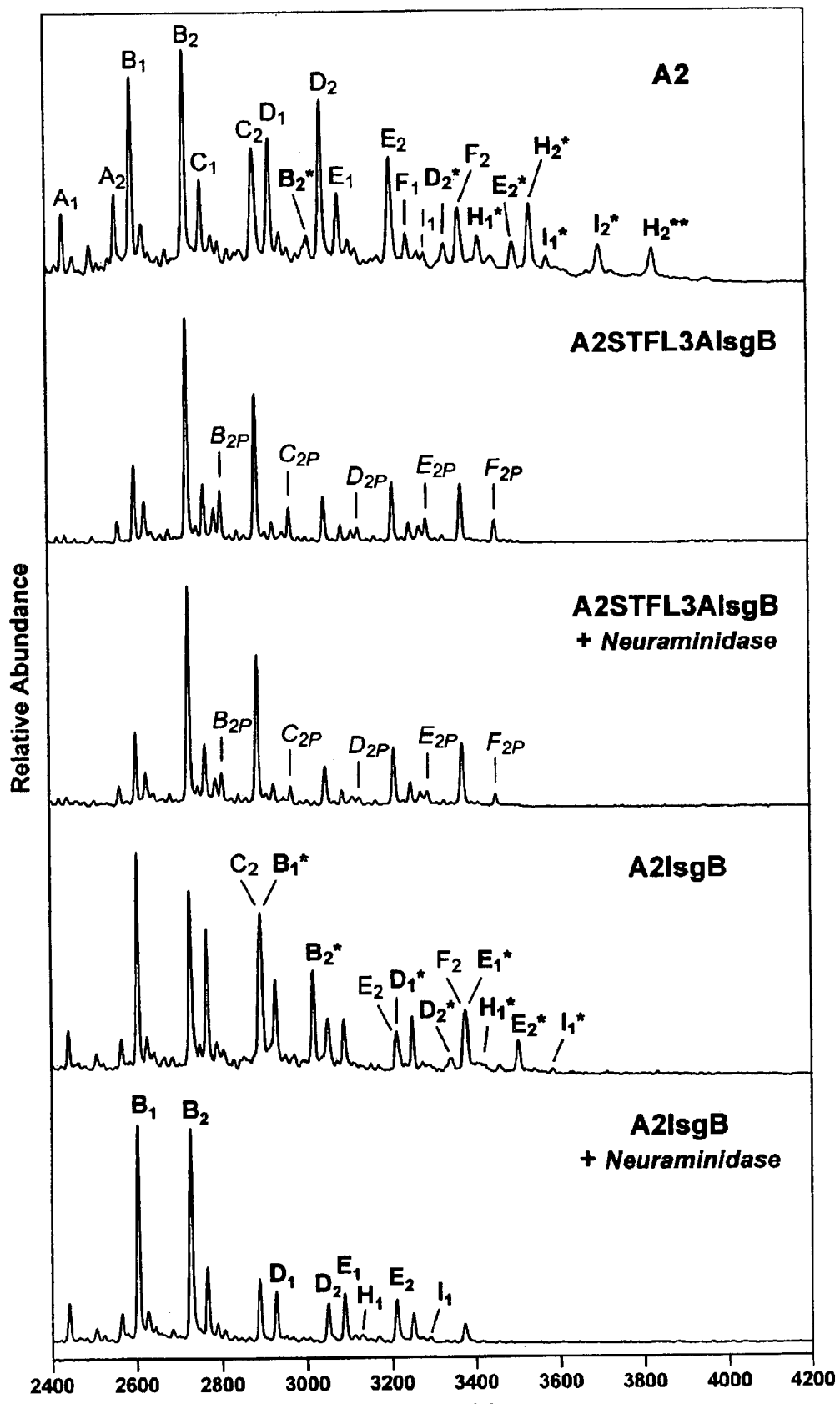
FIG. 3 depicts negative ion MALDI-MS spectra of O-LOS from *H. influenzae* A2, A2lsgB, and A2STFL3AlsgB. Mass spectra are shown comparing LOS isolated from *H. influenzae* strains before and after treatment with neuraminidase. See Tables 2 and 4 for molecular weights and compositions. The asterisks indicate the addition of NeuAc, and the number of PEA moieties is denoted by subscript. Species present in strain A2STFL3AlsgB containing an additional phosphate moiety are labeled in italics, with the additional subscript "P."

MALDI-TOF Analysis of A2lsgB and A2STFL3AlsgB. The O-deacylated LOS from the lsgB mutant (A2lsgB) and the triple mutant (A2STFL3AlsgB) were analyzed by MALDI mass spectrometry, both before and after neuraminidase treatment (FIG. 3). The A2STFL3AlsgB triple mutant did not produce any of the sialylated LOS structures characteristic of the *H. influenzae* A2 strain, nor did it produce the novel sialylated species (K$_2$*, K$_3$*, L$_2$*, and L$_3$*) found in the siaA mutant (FIG. 1) and the siaA and lic3A double mutant (FIG. 2). Additionally, the asialo forms of the novel acceptors (K$_2$, K$_3$, L$_2$, and L$_3$) were not detected in the A2STFL3AlsgB O-LOS population. The only LOS modifications observed involved a shift to higher phosphorylation states. In addition to an increase in the relative amount of glycoforms containing two PEAs, a formerly minor series of glycoforms containing two PEAs plus an additional phosphate moiety was prominent in the A2STFL3AlsgB O-LOS population (FIG. 3). As this new series nearly coincided with some of the predicted masses for the asialo N-acetylhexosamine containing glycoforms ($H_1$, $H_2$, $I_1$, and $I_2$), the A2STFL3AlsgB O-LOS was dephosphorylated with aqueous HF and reanalyzed by MALDI mass spectrometry. No significant peaks for the asialo N-acetylhexosamine acceptors were revealed in the dephosphorylated mixture (data not shown).

Like the A2STFL3AlsgB triple mutant, the lsgB mutant (A21sgB) did not produce the asialo or sialylated forms of the novel LOS structures ($K_2$, $K_3$, $L_2$, and $L_3$) found in the siaA mutants (FIG. 3). Additionally, there was almost no detectable production of the sialyl-N-acetylhexosamine containing glycoforms ($H_1^*$, $H_2^*$, $H_2^{**}$, $I_1^*$, and $I_2^*$) characteristic of the parental strain A2 (FIG. 3). Only very minor peaks for the $H_1^*$ and $I_1^*$ glycoforms were detected by MALDI mass spectrometry. It was not possible to detect the asialo glycoforms of these acceptors ($H_1$, $H_2$, $I_1$, and $I_2$) in the A21sgB O-LOS mixture, but small peaks for the $H_1$ and $I_1$ acceptors were distinguished after neuraminidase treatment (FIG. 3). While showing reduced production of the N-acetylhexosamine containing glycoforms, the A21sgB mutant was capable of expressing the hexose containing sialylated species ($B_1^*$, $B_2^*$, $D_2^*$, $E_1^*$, and $E_2^*$) found in *H. influenzae* A2.

Figure 4:
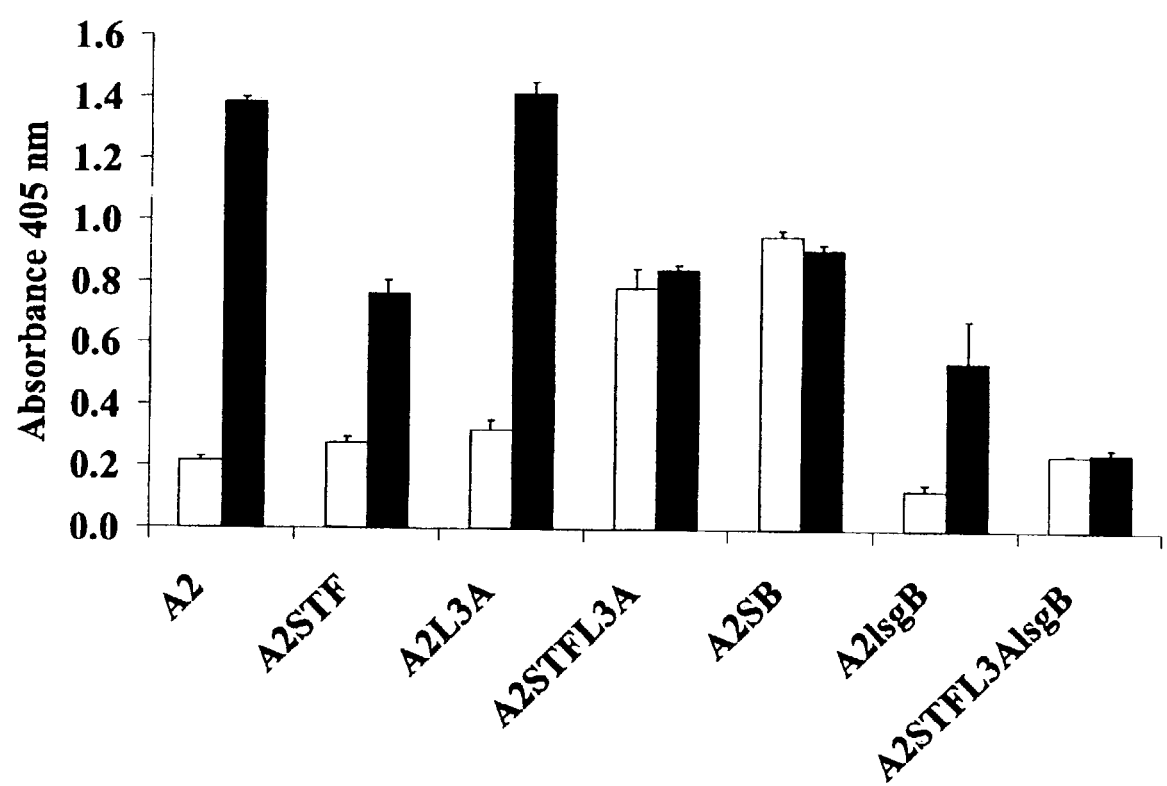
FIG. 4 depicts measurement of the level of LOS sialylation on terminal N-acetyllactosamine using 3F11. The monoclonal antibody 3F11 recognizes a terminal N-acetyllactosamine structure on the LOS. The presence of NeuAc on the N-acetyllactosamine structure inhibits the binding of 3F11. Sialic acid was removed from the LOS with neuraminidase. The level of sialylation was measured by comparing the samples before and after enzymatic treatment. The samples were measured at a 1:40 dilution of 3F11. Clear bars represent samples before treatment with neuraminidase, and solid bars represent samples after treatment with neuraminidase.

Whole-cell 3F11 ELISA. To more directly measure the level of sialylation of N-acetyllactosamine structures on the LOS of whole bacteria, a whole-cell ELISA assay was developed using the monoclonal antibody 3F11 (FIG. 4). Because of the relatively low abundance of the sialylated glycoforms, this method gives greater sensitivity in the analysis of the N-acetyllactosamine terminating glycoforms. The parent strain A2, in the absence of neuraminidase, bound 3F11 poorly (FIG. 4). When neuraminidase was added, 3F11 was able to bind with much greater efficiency, indicating the terminal N-acetyllactosamine containing glycoforms were substituted with NeuAc. Previous work by Hood et al. (Hood et al., 1999) showed that a mutation in siaB, a CMP-NeuAc synthetase, eliminated sialylation. When a siaB mutant (A2SB) was analyzed with this assay, the binding of 3F11 indicated that all the N-acetyllactosamine was free of NeuAc, however, the binding was approximately 50% of that seen in strain A2 after neuraminidase treatment (FIG. 4). This indicated that in the absence of sialylation, a population of the terminal N-acetyllactosamine was modified. In support of this, the MALDI-MS analysis of strain A2SB contained no sialylated glycoforms, but did contain higher molecular weight glycoforms not found in strain A2 (Phillips, Jones, Nichols, Apicelle and Gibson, unpublished data). The siaA mutant strain (A2STF), before neuraminidase treatment, reacted with 3F11 in a similar fashion as strain A2 before treatment with neuraminidase. After neuraminidase treatment, 3F11 binding to A2STF was reduced 50% of that seen when neuraminidase treated strain A2 was the target antigen. This decrease in binding between the neuraminidase treated samples was similar to the difference in the level of binding between strain A2SB and the neuraminidase treated strain A2 (FIG. 4). This suggests that in strain A2STF, a population of the terminal N-acetyllactosamine was sialylated and an additional population was modified, similar to that observed with strain A2SB. The MALDI-MS data from strain A2STF supports the hypothesis that other sugars are added to the terminal N-acetyllactosamine. LOS from strain A2STF had a reduced amount of the sialylated N-acetylhexosamine containing glycoforms ($H_1^*$, $H_2^*$, $I_1^*$, and $I_2^*$) when compared to the parental strain A2 (FIG. 1, Table 3). This change was not accompanied by an increase in the acceptor glycoforms ($H_1$, $H_2$, $I_1$, and $I_2$), but rather higher molecular weight glycoforms ($K_2^*$, $K_3^*$, $L_2^*$, and $L_3^*$) that were extended by a HexNAc and a PEA moiety when compared to glycoforms $H_1^*$, $H_2^*$, $I_1^*$, and $I_2^*$. Further evidence that sugars are being added to the terminal N-acetyllactosamine comes from analysis of strain 276.4STF, which indicates that in a siaA mutant, the sugars are added to the terminal N-acetyllactosamine structure (data not shown).

Data herein combined with a previous study by Hood et al. (Hood et al., 2001) indicate that *H. influenzae* contains multiple sialyltransferases. It is conceivable that in the absence of one sialyltransferase, the other sialyltransferase could compensate by sialylating terminal structures not normally sialylated in the parental strain. The lic3A mutant (A2L3A), which has been shown previously to be a sialyltransferase capable of sialylating both lactose and N-acetyllactosamine structures in vitro, but only lactose structures in vivo (Hood et al., 2001), was analyzed. Using the ELISA assay, strain A2L3A was similar to strain A2, regardless of neuraminidase treatment (FIG. 4). This indicated that lic3A was not responsible for sialylating N-acetyllactosamine structures in the parent strain A2. A double mutant in both siaA and lic3A (A2STFL3A) was analyzed before and after neuraminidase treatment. The binding of 3F11 was identical both before and after treatment with neuraminidase, and was approximately 50% of that seen with the neuraminidase treated parental strain A2 (FIG. 4). This result indicated that strain A2STFL3A lacked NeuAc on the terminal N-acetyllactosamine, and in a similar fashion to both strains A2SB and A2STF, a population of the terminal N-acetyllactosamine was further modified. The MALDI-MS analysis of strain A2STFL3A supports this contention (FIG. 2, Table 4). Strain A2STFL3A was completely devoid of the sialylated N-acetylhexosamine containing glycoforms representing peaks $H_1^*$, $H_2^*$, $I_1^*$, and $I_2^*$, but did contain peaks representing the acceptor glycoforms ($H_1$, $H_2$, $I_1$, and $I_2$). This strain also contained higher molecular weight N-acetylhexosamine containing glycoforms modified by the addition of a HexNAc and a PEA moiety ($K_2^*$, $K_3^*$, $L_2^*$, and $L_3^*$) when compared to the N-acetylhexosamine containing glycoforms designated by peaks $H_1^*$, $H_2^*$, $I_1^*$, and $I_2^*$. Both the ELISA assay and the MALDI-MS results of strain A2STFL3A indicated that the sialylation observed in the hexose containing glycoforms in strain A2STF was the result of the second sialyltransferase, Lic3A.

The 3F11 ELISA analysis of strain A21sgB showed lower binding activity, similar to A2 prior to neuraminidase (FIG. 4). After enzyme treatment, antibody binding to strain A21sgB increases four-fold, which is indicative of sialic acid release from N-acetyllactosamine. ELISA analysis of the triple mutant showed low levels of binding before and after neuraminidase treatment. This would indicate that all of the N-acetyllactosamine sites are not sialylated and that the levels of this acceptor are very low. This is confirmed by the MALDI data which shows a disappearance of the sialylated glycoforms and an inability to identify N-acetyllactosamine containing glycoforms.

Discussion

The biosynthesis of LOS is a complex process (Kimura and Hansen, 1986; Kimura et al., 1987; Zwahlen et al., 1986; Cope et al., 1990; Swords et al., 2000). Although previous investigations utilizing electrospray mass spectrometry revealed the presence of only two sialylated glycoforms in *H. influenzae* strain A2 (Phillips et al., 1996), the present MALDI-MS analysis of the LOS isolated from plate-grown organisms demonstrated eight LOS glycoforms terminating with NeuAc, including a disialylated species never observed before. This greater structural diversity of LOS seen in these MALDI-MS data can be attributed in part to advances made in mass spectrometry as well as an appreciation of the effects of glycoform biosynthesis when LOS is recovered from organisms grown on plates as opposed to broth culture (Gibson et al., 1997).

Both SiaA and LsgB function as sialyltransferases in *H. influenzae* strain A2. Both proteins have high amino acid identity to previously described sialyltransferases, but to no other known glycosyltransferases. The homologous Lst proteins in *H. ducreyi* and *Neisseria* have been shown to sialylate a terminal N-acetyllactosamine structure on their respective LOS (Bozue et al., 1999). Mutations in siaA and lsgB only affect the sialylation of N-acetyllactosamine containing glycoforms from stains A2 and 276.4. MALDI-MS analysis of LOS obtained from the siaA mutant strain A2STF showed that the sialylated N-acetyllactosamine containing glycoforms that are composed of six and seven hexoses disappear, and are replaced by a new set of sialylated glycoforms that are extended by the addition of a HexNAc and a PEA moiety. In order to eliminate the possibility that the effects seen by a mutation of siaA were caused by polar effects on downstream genes, the mutant was complemented. A construct was developed to allow insertion of a functional siaA gene into the chromosome at a putative intergenic region. The LOS and ELISA profiles of the complemented mutant strain A2STFC.P4 were identical to the parental strain A2 (FIG. 1, Table 3). This is clear evidence that the effects seen from the siaA mutants are the result of the inactivation of the siaA gene.

The most likely explanation for the observation of novel sialylated glycoforms is that, in the absence of sialylation by SiaA, the HexNAc and PEA are added to the oligosaccharide branch and this new terminal structure is modified by sialic acid by yet another sialyltransferase (LsgB). Alternatively, it is possible that in the absence of SiaA, the HexNAc and PEA are added to a terminal branch other than the one containing sialic acid. The SDS-PAGE analysis of strain 276.4 and its siaA mutant strain 276.4STF show this is not the case (data not shown). *H. influenzae* contains a tri-heptose core, and branched structures can be assembled from any of the three heptoses (Phillips et al., 1993; Risberg et al., 1999; Masoud et al., 1997). Strain 276.4 contains a mutation in lsgE, which results in a very defined LOS phenotype containing a single sialylated glycoform where the NeuAc extends from a terminal N-acetyllactosamine structure (Phillips et al., 1996). The siaA mutant strain 276.4STF contains only a very small amount of this glycoform, but also produces a higher molecular weight sialylated glycoform extended by the addition of one HexNAc and one PEA moiety (Table 5). This extended glycoform did not bind to monoclonal antibody 3F11 after neuraminidase treatment, indicating that the 3F11 N-acetyllactosamine epitope had been modified, by the addition of the extra moieties.

Analysis of the strains with a whole-cell ELISA assay using 3F11 (FIG. 4) revealed that the parental strain A2 binds 3F11 minimally before neuraminidase treatment, but after treatment with neuraminidase the binding of 3F11 increased considerably. This indicates that terminal N-acetyllactosamines were sialylated. Strain A2STF reacted in a similar fashion to strain A2, with the exception that the level of 3F11 binding after neuraminidase treatment was about 50% that of strain A2. This indicated that either the 3F11 positive glycoforms were not being produced in as great a quantity or that the 3F11 epitope was being modified. The difference in 3F11 binding of strain A2STF LOS before and after neuraminidase treatment indicated that even though there was a decrease in the expression of the terminal N-acetyllactosamine epitope in this strain, it was still capable of being sialylated. A mutation in lic3A did not affect sialylation of N-acetyllactosamine as compared to the parent strain A2 using ELISA, but there was no sialylation detected in the siaA and lic3A double mutant by ELISA (FIG. 4). The level of 3F11 binding in the siaA and lic3A double mutant was the same as that of the neuraminidase treated A2STF strain and a sialylation deficient siaB mutant strain (A2SB) (Hood et al., 1999). Hood et al. showed that a mutation in siaB, a CMP-NeuAc synthetase gene, eliminated sialylation in NTHi strains (Hood et al., 1999). MALDI-MS of the LOS from this double mutant showed the presence of sialylated hexosamine containing glycoforms. The failure of 3F11 to recognize these neuraminidase treated glycoforms most probably reflects the fact that these new glycoforms have been altered in such a way that this antibody cannot bind. The appearance of novel HexNAc and PEA-containing higher molecular weight glycoforms observed by MALDI-MS supports the hypothesis that the previously available acceptor for sialic acid, N-acetyllactosamine, is modified.

The presence of higher molecular weight sialylated species in the siaA and lic3A double mutant indicated that there had to be a third sialyltransferase in this system. The only other gene in *H. influenzae* with identity to a known sialyltransferase is lsgB. The LOS of the siaA, lic3A, and lsgB triple mutant (strain A2STFL3AlsgB) did not contain any sialylated glycoforms and did not produce any sialylated N-acetyllactosamine-containing glycoforms when analyzed with the ELISA assay (FIGS. 3 and 4), confirming LsgB as the third sialyltransferase.

LsgB would predictably have a different acceptor specificity from lactose or N-acetyllactosamine, since these structures are recognized by either lic3A or siaA. The siaA mutants have a HexNAc and a PEA moiety added to their structures, and in the case of 276.4STF, this eliminates the N-acetyllactosamine epitope (data not shown). To assess the structures of the novel acceptors in the siaA mutants, a series of exoglycosidase treatments on 276.4STF O-LOS were conducted. Mass spectrometric measurements indicated that that glycoform was related to the sialyl-N-acetyllactosamine containing glycoform in strain 276.4 O-LOS by the addition of a HexNAc and a PEA moiety. Enzymatic digestions conducted on the 276.4STF O-LOS suggested that these structural pieces formed a new branch on the sialylated terminus. Once the sample was dephosphorylated, it could lose a nonreducing terminal α-GalNAc by treatment with α-N-acetylgalactosaminidase, suggesting that the added PEA moiety had been linked to the α-GalNAc residue. This α-GalNAc could be released from the acceptor both before and after desialylation, indicating that it was not the sugar being sialylated. Treatment of the species lacking α-GalNAc with β-galactosidase had no effect, whereas neuraminidase treatment followed by β-galactosidase treatment confirmed that the sialic acid was attached to a β-linked Gal residue. These findings suggest that the terminal galactose of the N-acetyllactosamine moiety found in the 276.4 O-LOS is glycosylated with both a sialic acid and a α-GalNAc bearing a PEA group in the novel extended acceptor expressed in strain 276.4STF O-LOS. Further experiments are in progress to fully characterize this unusual branched structure and the related sialylated glycoforms in strains A2STF and A2STFL3A.

Little is known about the role of NeuAc in regulation of LOS biosynthesis in *Haemophilus*. Results herein indicate that in the absence of sialylation of terminal N-acetyllactosamine-containing glycoforms, they are being modified by the addition of a GalNAc and a PEA moiety. Vimr et al. demonstrated using an aldolase deficient NeuAc mutant that the level of sialylation was increased as compared to the parental strain (Vimr et al., 2000). In this same study, it was observed that in defined media lacking NeuAc, the LOS on the bacteria lacked both sialylation and the 3F11 epitope. When NeuAc was added to the defined media, the 3F11 epitope was restored and the LOS was sialylated. The two possibilities that could explain this phenomena are either lack of expression of the terminal N-acetyllactosamine containing glycoform, or a modification of this glycoform, eliminating the 3F11 epitope. SDS-PAGE and MALDI-MS analysis herein suggests that the latter explanation is true.

Sialylation has been studied in other mucosal pathogens, and its effects have varied from species to species. Sialylation in *N. gonorrhoeae* has probably been the most extensively studied of the mucosal pathogens. A single sialyltransferase has been identified in this organism, which requires an exogenous supply of CMP-NeuAc to sialylate its LOS (Nairn et al., 1988; Gilbert et al., 1996; Parsons et al., 1988; Parsons et al., 1993). *N. meningitidis* contains two sialyltransferases, one for its poly-NeuAc capsule (Edwards et al., 1994), which is found in all pathogenic strains, except serogroup A, and one responsible for sialylation of the LOS (Gilbert et al., 1996). Both *N. meningitidis* and *N. gonorrhoeae* use a terminal N-acetyllactosamine as their NeuAc acceptor, but the sialyltransferase can use a number of different acceptor structures in vitro (Mandrell et al., 1999; Gilbert et al., 1996; Gilbert et al., 1997). The Neisserial sialyltransferases have identity to lsgB, which is found in the lsg locus of *H. influenzae* (Phillips et al., 2000). Results presented here indicate that lsgB encodes a third sialyltransferase in this organism.

*C. jejuni* produces a number of sialylated lipopolysaccharide (LPS) glycoforms, some of which mimic human gangliosides (Gilbert et al., 2000; Aspinall et al., 1994; Guerry et al., 2000; Moran et al., 1991; Prendergast et al., 1998). Two sialyltransferases genes have been identified in *C. jejuni*: cstI and cstII (Gilbert et al., 2000). Both enzymes have high homology to one another, but have different acceptor and linkage specificities. CstII is a bifunctional enzyme, responsible for both the transfer of NeuAc to terminal galactose residues as well as the O-8 position of terminal NeuAcs. The *H. influenzae* lic3A gene is 40% homologous at the protein level to cstII (Hood et al., 2001). Hood et al. showed that this enzyme from *Haemophilus* is capable of transferring NeuAc to a terminal lactose or a N-acetyllactosamine acceptor in vitro, but they reported that it is unable to modify more than one site on the LOS in vivo (Hood et al., 2001). The results with MALDI-MS using strain A2L3A indicate this gene is involved in the formation of a disialylated glycoform in strain A2 (FIG. 3, Table 4).

In summary, three sialyltransferases with different specificities, lic3A, siaA, and lsgB, are involved in the sialylation of LOS glycoforms in *H. influenzae* strain A2. When siaA is mutated, LOS biosynthetic pathways are altered such that a novel acceptor is formed that can be sialylated by LsgB. The presence of such redundancy to sialylate LOS structures in *H. influenzae* underscores the complexity of the system and indicates an important role for sialylation in the survival of this opportunistic pathogen.

REFERENCES

Abdillahi and Poolman, *FEMS Microbiology Letters*, 48, 367-371 (1987).
Alexeyev, *Biotechniques*, 18, 52, 54, 56 (1995).
Aspinall et al., *Infection & Immunity*, 62, 2122-2125 (1994).
Borovkov et al., *Biotechniques*, 22, 812-814 (1997).
Bozue et al., *Journal of Biological Chemistry*, 274, 4106-4114 (1999).
Campagnari et al., *Infection & Immunity*, 55, 882-887 (1987).
Cope et al., *Infection & Immunity*, 58, 2343-2351 (1990).
Edwards et al., *Molecular Microbiology*, 14, 141-149 (1994).
Fleischmann et al., *Science*, 269, 496-512 (1995).
Gibson et al., *Journal of American Society for Mass Spectromery*, 8, 645-658 (1997).
Gilbert et al., *European Journal of Biochemistry*, 249, 187-194 (1997).
Gilbert et al., *Journal of Biological Chemistry*, 271, 28271-28276 (1996).
Gilbert et al., *Journal of Biological Chemistry*, 275, 3896-3906 (2000).
Guerry et al., *Infection & Immunity*, 68, 6656-6662 (2000).
Herriott et al., *Journal of Bacteriology* 101, 517-524 (1970).
Hitchcock and Brown, *Journal of Bacteriology*, 154, 269-277 (1983).
Hood et al., *Molecular Microbiology*, 22, 951-965 (1996).
Hood et al., *Molecular Microbiology*, 3, 679-692 (1999).
Hood et al., *Molecular Microbiology*, 39, 341-351 (2001).
Inzana, *Journal of Infectious Diseases*, 148, 492-499 (1983).
Kimura and Hansen, *Infection & Immunity*, 51, 69-79 (1986).
Kimura et al., (1987) *Infection & Immunity*, 55, 1979-1986 (1987).
Lesse et al., *Journal of Immunological Methods*, 126, 109-117 (1990).
Mandrell et al., *Infection & Immunity*, 60, 1322-1328 (1992).
Mandrell et al., *Journal of Experimental Medicine*, 168, 107-126 (1988).
Maskell et al., *Molecular Microbiology*, 5, 1013-1022 (1991).
Masoud et al, *Biochemistry*, 36, 2091-2103 (1997).
Menard et al., *Journal of Bacteriology*, 175, 5899-5906 (1993).
Moran et al., *Journal of Bacteriology*, 173, 618-626 (1991).
Nairn et al., *Journal of General Microbiology*, 134, 3295-3306 (1988).
Parsons et al., *Microbial Pathogenesis*, 14, 329-335 (1993).
Parsons et al., *Microbial Pathogenesis*, 5, 303-309 (1988).
Patrick et al., *Infection & Immunity*, 55, 2902-2911 (1987).
Phillips et al., *Biochemistry* 32, 2003-2012 (1993).
Phillips et al., *Biochemistry*, 35, 5937-5947 (1996).
Phillips et al., *Journal of Biological Chemistry*, 275, 4747-4758 (2000).
Prendergast et al., *Infection & Immunity*, 66, 3649-3655 (1998).
Risberg et al., *European Journal of Biochemistry* 261, 171-180 (1999).
Sambrook and Russell, *Molecular Cloning: A Laboratory Manual*, Cold Spring Harbor Press, Cold Spring Harbor, N.Y. (2001).
Schneider et al., *Journal of Experimental Medicine*, 174, 1601-1605 (1991).
Spinola et al., *Infection & Immunity*, 58, 1558-1564 (1990).
Swords et al., *Molecular Microbiology*, 37, 13-27 (2000).

Towbin et al., *Proceedings of the National Academy of Sciences of the United States of America*, 76, 4350-4354 (1979).

Tsai and Frasch, *Analytical Biochemistry*, 119, 115-119 (1982).

Vimr et al., *Molecular Microbiology*, 36, 1113-1123 (2000).

Weiser et al., *Cell*, 59, 657-665 (1989) (Weiser et al. I).

Weiser et al., *Infection & Immunity*, 57, 3045-3052 (1989) (Weiser et al. II).

Weiser et al., *Journal of Bacteriology*, 172, 3304-3309 (1990).

Whitby et al., *FEMS Microbiology Letters*, 158, 57-60 (1998).

Yamasaki et al., *Molecular Microbiology*, 28, 1233-1242 (1991).

Zwahlen et al., *Microbial Pathogenesis*, 1, 465-473 (1986).

All publications, patents and patent applications are incorporated herein by reference. While in the foregoing specification this invention has been described in relation to certain embodiments, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated polynucleotide comprising SEQ ID NO:1.

2. The isolated polynucleotide comprising nucleotides 2538-3452 of SEQ ID NO:1.

3. An expression cassette comprising the isolated polynucleotide of claim 1 or claim 2.

4. An isolated cell comprising the expression cassette of claim 3.

5. The cell of claim 4, further comprising an expression cassette comprising a nucleotide sequence encoding SEQ ID NO:4.

6. An isolated lipooligosaccharide (LOS) production cell comprising:
   (i) a nucleic acid encoding SEQ ID NO:4;
   (ii) the expression cassette of claim 3;
   (iii) an acceptor molecule; and
   (iv) a substrate for a sialyltransferase.

7. The production cell of claim 6, wherein the cell is a gram negative bacterium.

8. The production cell of claim 7, wherein the bacterium is *Haemophilus influenzae* or *Escherichia coli*.

9. An isolated polynucleotide comprising a nucleic acid sequence, wherein the nucleic acid sequence encodes SEQ ID NO:3.

10. An expression cassette comprising the isolated polynucleotide of claim 9.

11. An isolated cell comprising the expression cassette of claim 10.

12. The cell of claim 11, further comprising an expression cassette comprising a nucleotide sequence encoding SEQ ID NO:4.

13. An isolated lipooligosaccharide (LOS) production cell comprising:
   (i) a nucleic acid encoding SEQ ID NO:4;
   (ii) the expression cassette of claim 10;
   (iii) an acceptor molecule; and
   (iv) a substrate for a sialyltransferase.

14. The production cell of claim 13, wherein the cell is a gram negative bacterium.

15. The production cell of claim 14, wherein the bacterium is *Haemophilus influenzae* or *Escherichia coli*.

* * * * *

SEQUENCE LISTING

<160> NUMBER OF SEQ ID NOS: 14

<210> SEQ ID NO 1
<211> LENGTH: 4348
<212> TYPE: DNA
<213> ORGANISM: Haemophilus influenzae

<400> SEQUENCE: 1

```
cagcggcaag aaatataggg ttagaaaaag cacaaggtga ctatattaca ttcttagata      60
gtgatgattt tattgcaaat gataaattag aaaaacaact taattttatg ttgcaaaatc     120
atcttgtaat gacgcatggc aactatgctt tctgtgattt ggaaggaaat cagataaaat     180
tagttacgac tagtaaaaaa attgattatt taaccttatt acaaggtaac caatttaaaa     240
taatgaccgt acttgttaaa agagaatcta ttaaattact taggtttcct aatattaaac     300
acgaagatta tgccttcttt ttagattgtt taaaagaagt taaacaatct atactatata     360
gccatcaggc aagttcattt gtaagaatag gtaaagtcag cgtttcatca aataaattta     420
aaagtgcaat ctggacattt aatatctatt ttaaaagaga gaaactaggt gtagtaaaat     480
caatttatta ttttatcctc tatgcctata atggatttat taaatacaag aaataaaaat     540
atgatttcat tacttattat tagcttcggg cgttgtcaag aagtattgga aacgtttgca     600
tgtgtcaata aatatcatgg taaaaaaatt gaattacttt tccttgataa taatccagca     660
agagagttgg aaacagctct atcttctatt gtagaaaata atagtagcat tttatttagc     720
tattttcata ccggtgagaa tctaggtgtt gctgaaggac gtaatttttt aattgaaaaa     780
gctcaaggag atattttaat tacacttgat gacgatattg aaattgaaga tattattctt     840
ttaattcaga aagtgactga ttatatggca aataatgcta agtaggagc gttagccttt     900
aatattaaaa actatttttac tcgtaaagca ttatcacacg agatcccaca tggtaataaa     960
aagttagatt tttcacagaa tttactgact tattatttta ttggtgctgg gcatgcaata    1020
aggaaagaag tctatcaaaa agcggggttt taccctaagg atcttggcct atatggtggt    1080
gaagaaagag atttgtcatt taggacttta gaagcaggct atcagatact ttatgcaagt    1140
gatattgtga tttatcataa ggtttcacca aatggaagaa tgatgagaaa aaaggaaaac    1200
ttctttagat atagaaatca acttattgtt ttaaatagat atatgccaat gagatatcga    1260
ttaacttcta attttgtttg gtctattttt tatcttgtaa aaatgaacgg agaaattcta    1320
gatattgtaa aagtattatc agaaattttt agtttaaaaa gaaaggtagt atcagataaa    1380
acaattagat atattaaatt tgttgatggt agattatatt attaatgatt atttgattgg    1440
tattatttt atttatttct ctttcttcgt tgatgggtt aaaatataat aaattatcta     1500
```

-continued

```
gccaactctt tatttttaat attttaatta tctattttt ttactgtttt tagatatggc    1560
gtaggtgaag agtattttca atatgaagaa ttatttaaac aagtgttacc aataaataag    1620
atatcaattt cttattttaa ggataatgtt catgatattg agtatggtta tttgttttt    1680 gaatcagtaa ttaaatactt tactgatgaa caccttgttt ttcttgtttt ttatgtcttt    1740
gcaatgttcc ttttctata taaggcaata aacaatactg gttatatag aaatatacag    1800 ttgcttattt tctattcttt tatattttta gaatatattt ttagtgtgca cagacaaggt    1860
gtggcaatgt gcataatata ttatgctatc atactgatcc atgaggataa attatttagt    1920
atactttgct ggttatttta gcctcgctat ttcataagat agccattata cttattccgc    1980 tttattttt tataagaaaa gaatttaaag tatctgttct attttacatg gttgtaattg    2040
cattatttat atcttctttt gacttaatag gtatggttat taagtggtgt aatgagaatt    2100
tctctaatgt ggctgttttt agatgggtgt tcactatta ttttaataag catgatgcaa    2160
atttaaaaat gtctgctata ccttacatgc aacgagcaat aatgttattt atactattcc    2220 tatttttataa aagaatcccc tatacttatt ctaacttact gctcttatat gttagtcttt    2280
tctttatatt ctcctaatgtg ggagtgttag caaataggg ttcaggaatt ttattggtat    2340
cttatgcaat attttctct gttctaattt gtaacttaaa atttaagaga atagattac    2400 ttattatttt atatatgttt tttctaactt agtattttg ttaagaatat tcatgatgtt    2460
catccgttaa ctaataagct aaattatttg ctatatgaat taaactataa gacagttaac    2520
atatttcagg aggggaatg aataaaagag taataattat cagtaatatg aggatgttat    2580
ttttatttct tcttatagat aaaggagag taggggatgt tttatatttt tctaataaag    2640
ttgaatctaa aattaaatct gcatttgagt ttcatagtgc tgattctatc tttgatttac    2700
tatttaaaaa aattatttct gaaattaaat taatatatt ttgttataaa aataaaatag    2760
aatttaaaaa aactgttgtt tatggtgctg accatatttt aggctcttca ttttttttaa    2820
gtaaatgtct ttttattta attgaagatg gcactgagaa ctatcaaact aaaaattata    2880
aaagaagttt aaaaaataga ttgttttcac tacctaaatt tggaatgcat aaaaatgtta    2940
agaaaattta tttaacaagg aatgataata ttcctgattg tattaaagaa aaagttgaag    3000
taattaatat tcatcaactt tggaaaaata aaacaaaaga agaacaagat gagattttat    3060
ttttactaag tgtagataaa aataaattag aaaatttaaa gcataaaagt atcgttttat    3120
ttacacagcc actttcagaa gataatgttt taactgagga agagaaaatc gctctttata    3180
aaactataat aggaaattat gatcaagaga aacttgtaat taaaacacat ccaagagaaa    3240
ctacaaacta tcgaaattat ttccctaata ttgaggtttt tagtgaaaat tacccatctg    3300 agatttaga tgtattaggc ataagatttg aaaagtggt aacaattttc tcaacggctg    3360
tatatgtata cccaaaagaa gatattattt tttatggtac aaaaatacac cctaaattat    3420
tatcaagatt tggaaggata gaatatgaat aagttatttt tgtctaaatt tattttagct    3480
ttattagatt ttattacatt taatgcttct ttttcattat ctttactaat aatatccta    3540 tatcatcatg gatatgatca atatttacct gtttacgaag tggatgatag atattacatt    3600
catacgcttt taggttttct ttgtgttgga tggtttgcta ttaggctaag acattatact    3660
tatagaaaac ctttttggtt tgagttaaaa gagattttta gaacacttct tatctttgcg    3720
gtctttgaac ttgcaattgt tgcattttct aaattatatt tctctagata tttatggttt    3780
cttacttggg gaatcacttt tctaattttc ccttttgcaa gagtatttgt aaagcattta    3840
```

-continued

```
ttaataaagc ttagttggtt tgttagaaat accgtcataa ttggtgctag agataatgct    3900
tttgatatat ataatgcctt gaaagatgaa ccttatttag gtttaaaggt aatatgtttt    3960
atttctgtat caaatactac taatgtcaat gtggtatcac tggatattcc tattttagat    4020
aatactgatt cttggaaatc aagaatgaag aagtcagatc aatttattat tgctcttgag    4080
gataatgaag aagtagatag gaataattgg ttacgttatt tttccacaaa tggatatcgt    4140
tctgtttctg ttattcctac attgagaggc ttacctttat atagtacgga catgtctttt    4200
atgtttagcc atgaaatgat gttattacga atgaataata atttggctaa actatcttct    4260
cgtattttga acgaaccat ggatattgtt gttggttcct tagctattat tatattttcc     4320
ccagtgttgc tttatctgta ttttgcag                                      4348
```

<210> SEQ ID NO 2
<211> LENGTH: 915
<212> TYPE: DNA
<213> ORGANISM: Haemophilus influenzae

<400> SEQUENCE: 2

```
atgaataaaa gagtaataat tatcagtaat atgaggatgt tattttttatt tcttcttata    60 gataaaagga gattagggga tgttttttata ttttctaata aagttgaatc taaaattaaa   120
tctgcatttg agtttcatag tgctgattct atctttgatt tactatttaa aaaaattatt   180
tctgaaatta aattaatata ttttttgttat aaaaataaaa tagaatttaa aaaaactgtt   240
gtttatggtg ctgaccatat tttaggctct tcattttttt taagtaaatg tcttttttat   300
ttaattgaag atggcactga gaactatcaa actaaaaatt ataaaagaag tttaaaaaat   360
agattgtttt cactacctaa atttggaatg cataaaaatg ttaagaaaat ttatttaaca   420
aggaatgata atattcctga ttgtattaaa gaaaaagttg aagtaattaa tattcatcaa   480
ctttggaaaa ataaaacaaa agaagaacaa gatgagagatt tatttttact aagtgtagat   540
aaaaataaat tagaaaattt aaagcataaa agtatcgttt tatttacaca gccactttca   600
gaagataatg tttaactga ggaagagaaa atcgctctt ataaaactat aataggaaat    660
tatgatcaag agaaacttgt aattaaaaca catccaagag aaactacaaa ctatcgaaat   720
tatttcccta atattgaggt ttttagtgaa aattacccat ctgagatttt agatgtatta   780
ggcataagat ttgaaaaagt ggtaacaatt ttctcaacgg ctgtatatgt atacccaaaa   840
gaagatatta tttttttatgg tacaaaaata caccctaaat tattatcaag atttggaagg   900
atagaatatg aataa                                                    915
```

<210> SEQ ID NO 3
<211> LENGTH: 304
<212> TYPE: PRT
<213> ORGANISM: Haemophilus influenzae

<400> SEQUENCE: 3

```
Met Asn Lys Arg Val Ile Ile Ser Asn Met Arg Met Leu Phe Leu
  1               5                  10                  15

Phe Leu Leu Ile Asp Lys Arg Arg Leu Gly Asp Val Phe Ile Phe Ser
                 20                  25                  30

Asn Lys Val Glu Ser Lys Ile Lys Ser Ala Phe Glu Phe His Ser Ala
             35                  40                  45

Asp Ser Ile Phe Asp Leu Leu Phe Lys Lys Ile Ile Ser Glu Ile Lys
         50                  55                  60

Leu Ile Tyr Phe Cys Tyr Lys Asn Lys Ile Glu Phe Lys Lys Thr Val
```

-continued

```
                65                  70                  75                  80
         Val Tyr Gly Ala Asp His Ile Leu Gly Ser Ser Phe Phe Leu Ser Lys
                             85                  90                  95
         Cys Leu Phe Tyr Leu Ile Glu Asp Gly Thr Glu Asn Tyr Gln Thr Lys
                            100                 105                 110
         Asn Tyr Lys Arg Ser Leu Lys Asn Arg Leu Phe Ser Leu Pro Lys Phe
                            115                 120                 125
         Gly Met His Lys Asn Val Lys Lys Ile Tyr Leu Thr Arg Asn Asp Asn
                    130                 135                 140
         Ile Pro Asp Cys Ile Lys Glu Lys Val Glu Val Ile Asn Ile His Gln
         145                 150                 155                 160
         Leu Trp Lys Asn Lys Thr Lys Glu Glu Gln Asp Glu Ile Leu Phe Leu
                            165                 170                 175
         Leu Ser Val Asp Lys Asn Lys Leu Glu Asn Leu Lys His Lys Ser Ile
                            180                 185                 190
         Val Leu Phe Thr Gln Pro Leu Ser Glu Asp Asn Val Leu Thr Glu Glu
                            195                 200                 205
         Glu Lys Ile Ala Leu Tyr Lys Thr Ile Ile Gly Asn Tyr Asp Gln Glu
                    210                 215                 220
         Lys Leu Val Ile Lys Thr His Pro Arg Glu Thr Thr Asn Tyr Arg Asn
         225                 230                 235                 240
         Tyr Phe Pro Asn Ile Glu Val Phe Ser Glu Asn Tyr Pro Ser Glu Ile
                            245                 250                 255
         Leu Asp Val Leu Gly Ile Arg Phe Glu Lys Val Val Thr Ile Phe Ser
                            260                 265                 270
         Thr Ala Val Tyr Val Tyr Pro Lys Glu Asp Ile Ile Phe Tyr Gly Thr
                            275                 280                 285
         Lys Ile His Pro Lys Leu Leu Ser Arg Phe Gly Arg Ile Glu Tyr Glu
                    290                 295                 300

<210> SEQ ID NO 4
<211> LENGTH: 304
<212> TYPE: PRT
<213> ORGANISM: Haemophilus influenzae

<400> SEQUENCE: 4

Met Asn Leu Met Leu Cys Cys Thr Pro Leu Gln Val Leu Ile Ala Arg
         1                   5                  10                  15
         Lys Ile Ile Glu Leu His Pro Asn Glu Gln Phe Phe Gly Val Met Phe
                             20                  25                  30
         Gly Gly Val Trp Asp Lys Lys Arg Thr Leu Tyr Ala Ser Lys Leu Ala
                             35                  40                  45
         Glu Val Cys Ser Asp Ser Met Asn Ile Asp Thr Gly Lys Asp Leu Lys
                    50                  55                  60
         Gly Phe Asp Phe Leu Lys Leu Met Arg Gln Leu Lys Asn Lys Ile Thr
         65                  70                  75                  80
         His Lys Gly Phe Asp Lys Val Phe Leu Ala Asn Leu Asn Ser Leu Trp
                             85                  90                  95
         Leu Gln Thr Tyr Leu Ser His Val Ser Phe Lys Glu Leu Tyr Thr Phe
                            100                 105                 110
         Asp Asp Gly Ser Asp Asn Ile Phe Pro His Pro Asn Leu Leu Arg Glu
                    115                 120                 125
         Pro Gly Thr Phe Lys Tyr Lys Leu Ile Lys Ala Phe Ile Gly Asp Lys
                    130                 135                 140
```

-continued

```
Tyr Ser Val Asn Lys Leu Phe Lys Lys Ile Lys Lys His Tyr Thr Val
145                 150                 155                 160

Tyr Pro Asn Tyr Lys Asn Ile Val Ser Asn Ile Glu Pro Ile Ser Leu
            165                 170                 175

Trp Asp Asn Gln Ile Asp Cys Glu Ile Asp Gly Glu Val Ser Phe Phe
        180                 185                 190

Ile Gly Gln Pro Leu Leu Asn Thr Lys Glu Glu Asn Ile Ser Leu Ile
    195                 200                 205

Lys Lys Leu Lys Asp Gln Ile Pro Phe Asp Tyr Tyr Phe Pro His Pro
210                 215                 220

Ala Glu Asp Tyr Arg Val Asp Gly Val Asn Tyr Val Glu Ser Glu Leu
225                 230                 235                 240

Ile Phe Glu Asp Tyr Val Phe Lys His Leu Ser Asn Lys Lys Ile Ile
                245                 250                 255

Ile Tyr Thr Phe Phe Ser Ser Val Ala Phe Asn Leu Leu Ser His Pro
            260                 265                 270

Asn Val Glu Ile Arg Phe Ile Arg Thr Ser Ile Pro Arg Trp Gln Phe
        275                 280                 285

Cys Tyr Asp Ser Phe Pro Asp Leu Gly Leu Thr Ile Tyr Lys Glu Ile
    290                 295                 300
```

```
<210> SEQ ID NO 5
<211> LENGTH: 30
<212> TYPE: DNA
<213> ORGANISM: Haemophilus influenzae

<400> SEQUENCE: 5
ctgcaaaata cagataaagc aacactgggg                                  30

<210> SEQ ID NO 6
<211> LENGTH: 31
<212> TYPE: DNA
<213> ORGANISM: Haemophilus influenzae

<400> SEQUENCE: 6
cagcggcaag aaatataggg ttagaaaaag c                                31

<210> SEQ ID NO 7
<211> LENGTH: 22
<212> TYPE: DNA
<213> ORGANISM: Haemophilus influenzae

<400> SEQUENCE: 7
gatgttattt ttattttgt ta                                           22

<210> SEQ ID NO 8
<211> LENGTH: 22
<212> TYPE: DNA
<213> ORGANISM: Haemophilus influenzae

<400> SEQUENCE: 8
acttagggtg tattttggtt cc                                          22

<210> SEQ ID NO 9
<211> LENGTH: 18
<212> TYPE: DNA
<213> ORGANISM: Haemophilus influenzae

<400> SEQUENCE: 9
cggactatca taacgggc                                               18
```

```
<210> SEQ ID NO 10
<211> LENGTH: 18
<212> TYPE: DNA
<213> ORGANISM: Haemophilus influenzae

<400> SEQUENCE: 10
ctcagaattc gggcttcg                                                 18

<210> SEQ ID NO 11
<211> LENGTH: 18
<212> TYPE: DNA
<213> ORGANISM: Haemophilus influenzae

<400> SEQUENCE: 11
agggggataa aacaaagg                                                 18

<210> SEQ ID NO 12
<211> LENGTH: 18
<212> TYPE: DNA
<213> ORGANISM: Haemophilus influenzae

<400> SEQUENCE: 12
ggcaagtccc tgttcaaa                                                 18

<210> SEQ ID NO 13
<211> LENGTH: 30
<212> TYPE: DNA
<213> ORGANISM: Haemophilus influenzae

<400> SEQUENCE: 13
atgtccaaaa gcagccaacc aaataaaccc                                    30

<210> SEQ ID NO 14
<211> LENGTH: 30
<212> TYPE: DNA
<213> ORGANISM: Haemophilus influenzae

<400> SEQUENCE: 14
caacgccgaa atcaacccaa atagaaagcc                                    30
```